United States Patent [19]

DuBose

[11] 4,061,469
[45] Dec. 6, 1977

[54] CALIBRATION IN A BLOOD ANALYZER

[75] Inventor: Charles Ray DuBose, Stafford, Tex.

[73] Assignee: Hycel, Inc., Houston, Tex.

[21] Appl. No.: 638,472

[22] Filed: Dec. 8, 1975

[30] Foreign Application Priority Data

| Dec. 6, 1974 | United Kingdom | 52815/74 |
| Dec. 6, 1974 | United Kingdom | 52810/74 |
| Dec. 6, 1974 | United Kingdom | 52811/74 |
| Dec. 6, 1974 | United Kingdom | 52812/74 |
| Dec. 6, 1974 | United Kingdom | 52813/74 |
| Dec. 6, 1974 | United Kingdom | 52814/74 |

[51] Int. Cl.² .................. G01N 33/16; G01N 21/24
[52] U.S. Cl. .................. 23/253 R; 356/39; 364/416
[58] Field of Search ............ 23/253 R, 230 R, 259 R, 23/230 B; 356/39, 36; 235/151.35

[56] References Cited

U.S. PATENT DOCUMENTS

| 3,697,224 | 10/1972 | Means ............................ 23/253 X |
| 3,725,204 | 4/1973 | Marshall, Jr. et al. ............ 23/253 X |
| 3,861,877 | 1/1975 | Matharani et al. ................ 23/253 X |
| 3,873,273 | 3/1975 | Moran et al. ..................... 23/259 X |
| 3,874,850 | 4/1975 | Sorensen et al. ................. 23/253 X |

Primary Examiner—R.E. Serwin
Attorney, Agent, or Firm—Robert P. Cogan; Timothy L. Burgess

[57] ABSTRACT

In a blood analyzer, improved calibration is provided. First and second photodetectors sense energy supplied directly from a source and from the source through a sample respectively. A log ratio amplifier provides an analog output indicative to the log of the ratio of the outputs of the photodetectors to a control circuit. When a blank sample is measured, a programmable voltage source operates to set the analog output to a selected level. A reference sample having optical density corresponding to a preset value is next measured, and a variable gain amplifier is set by the control circuit to cause the analog signal to correspond to the preset value.

10 Claims, 15 Drawing Figures

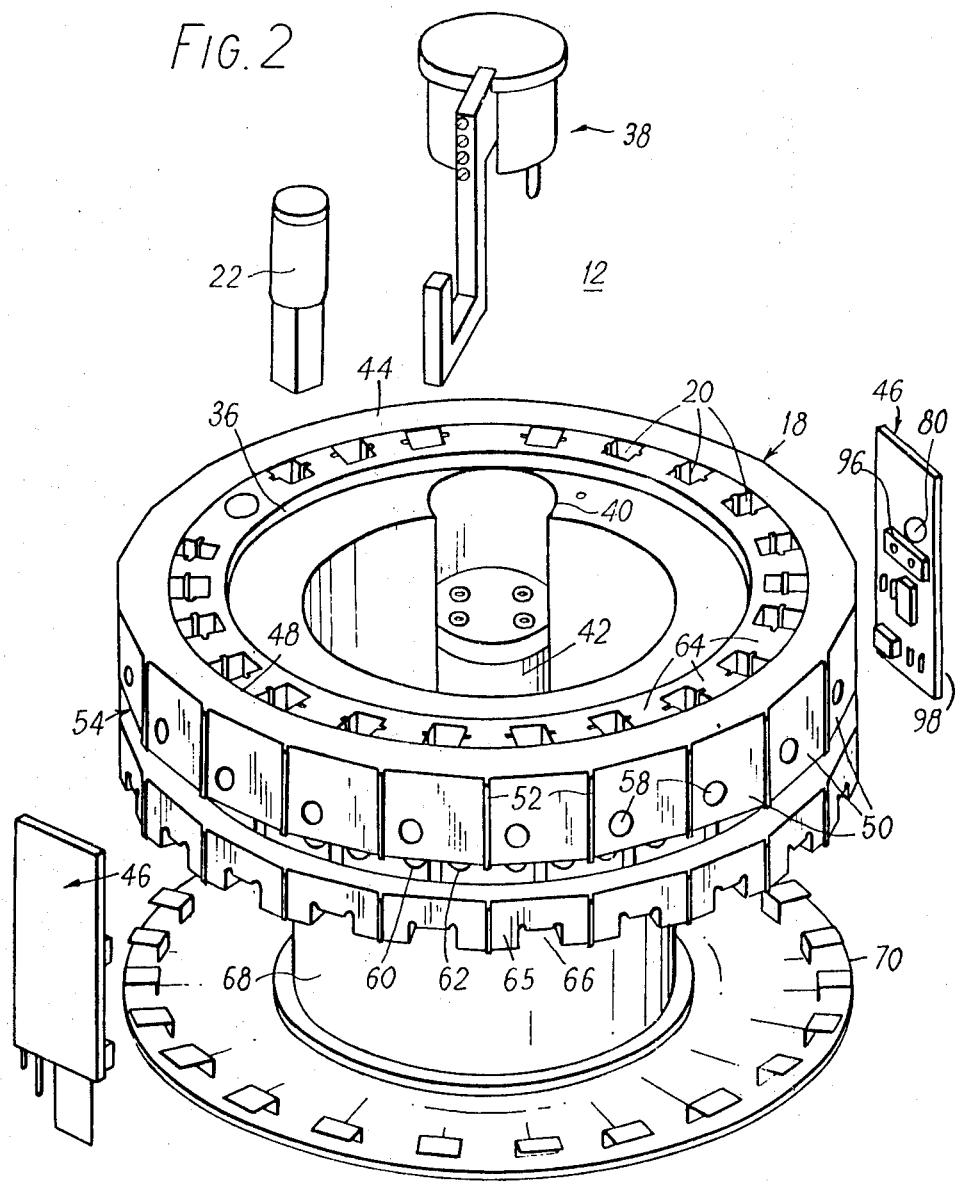

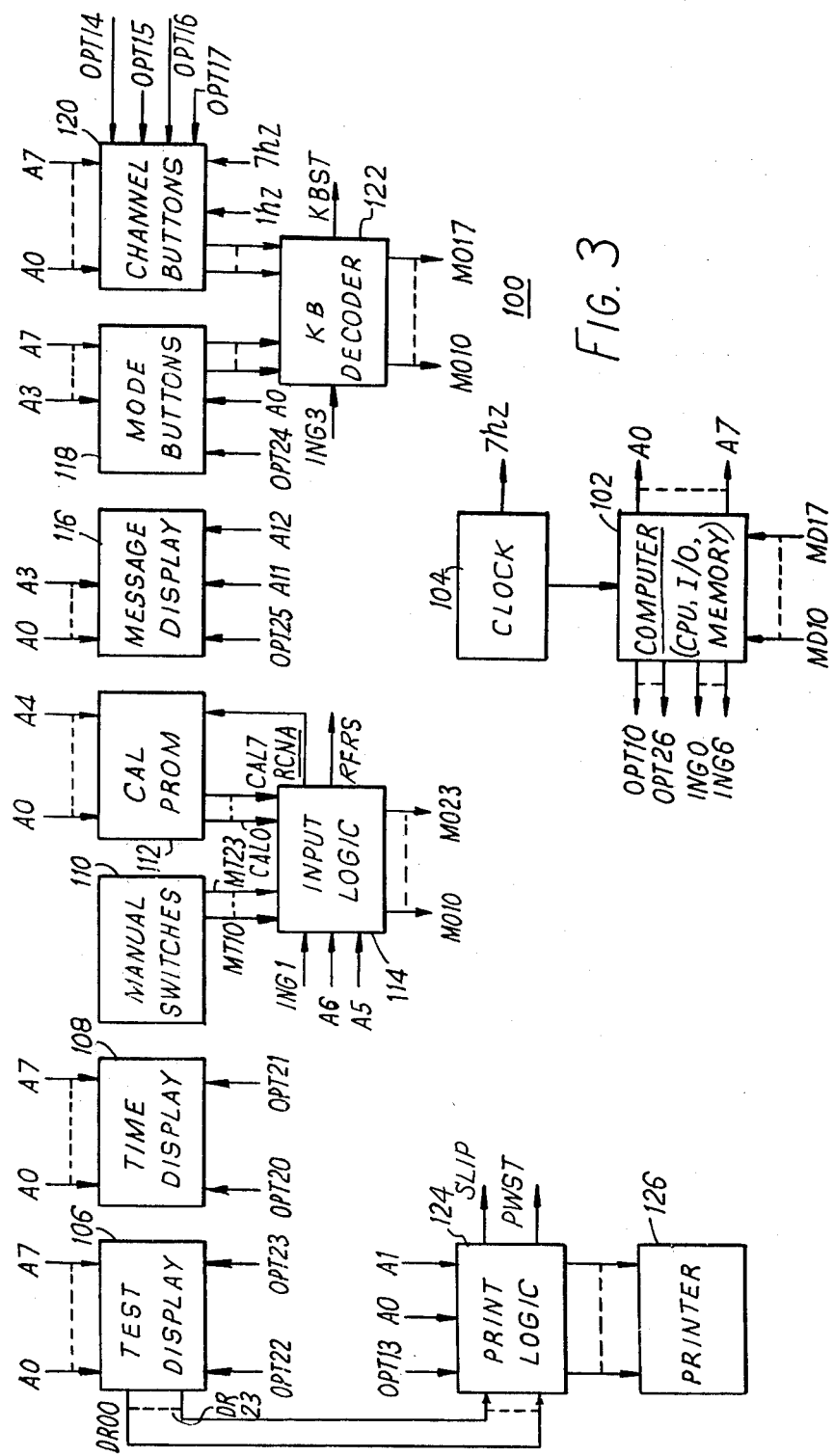

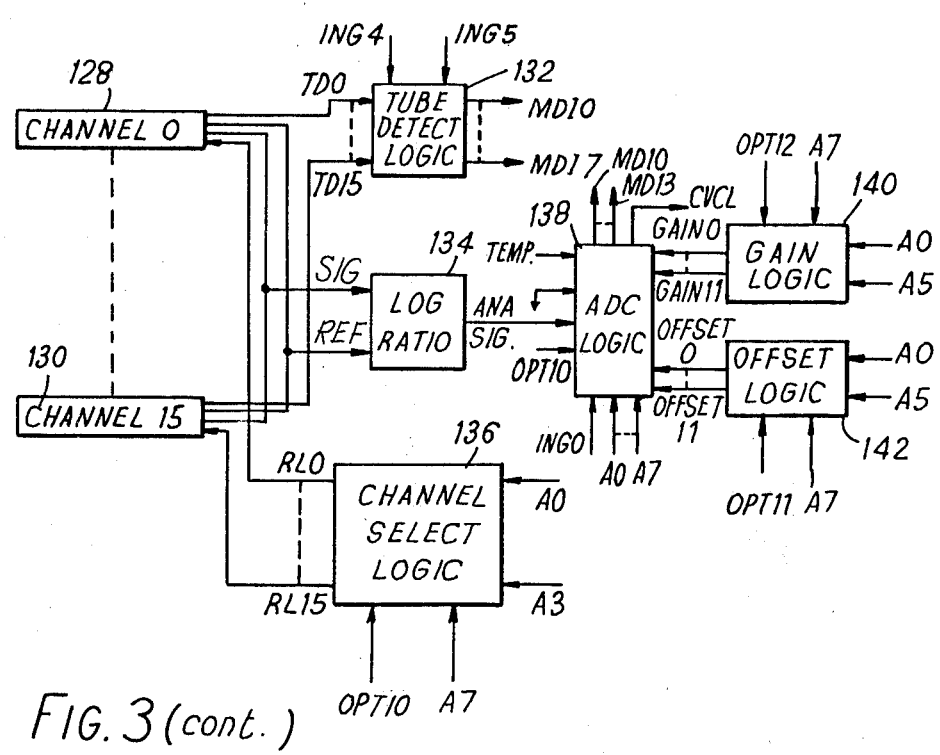
FIG. 3 (cont.)
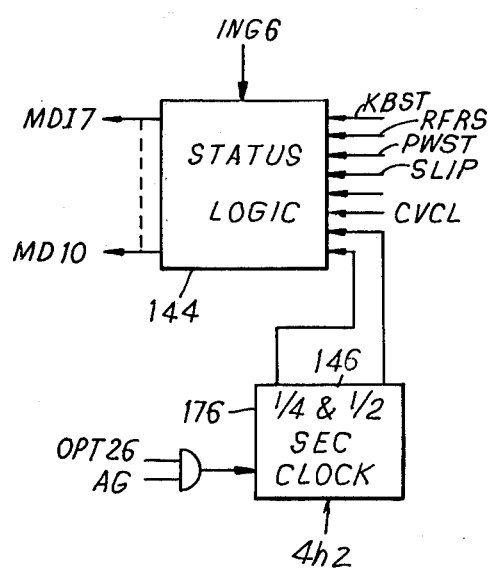

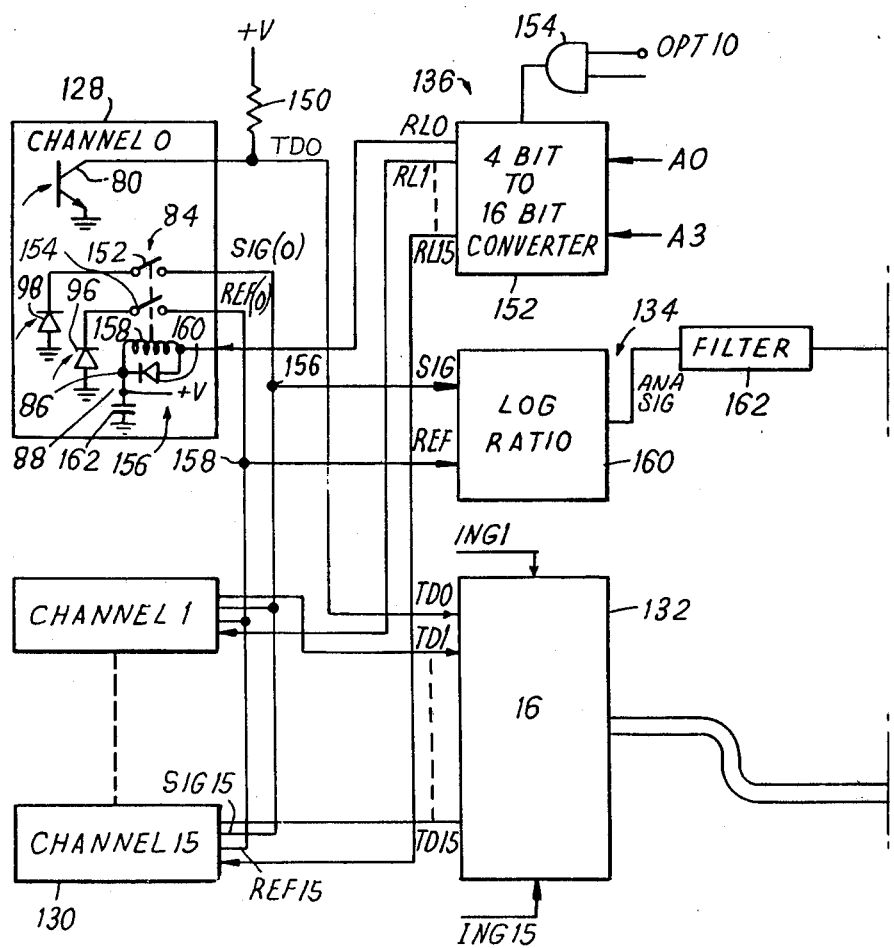

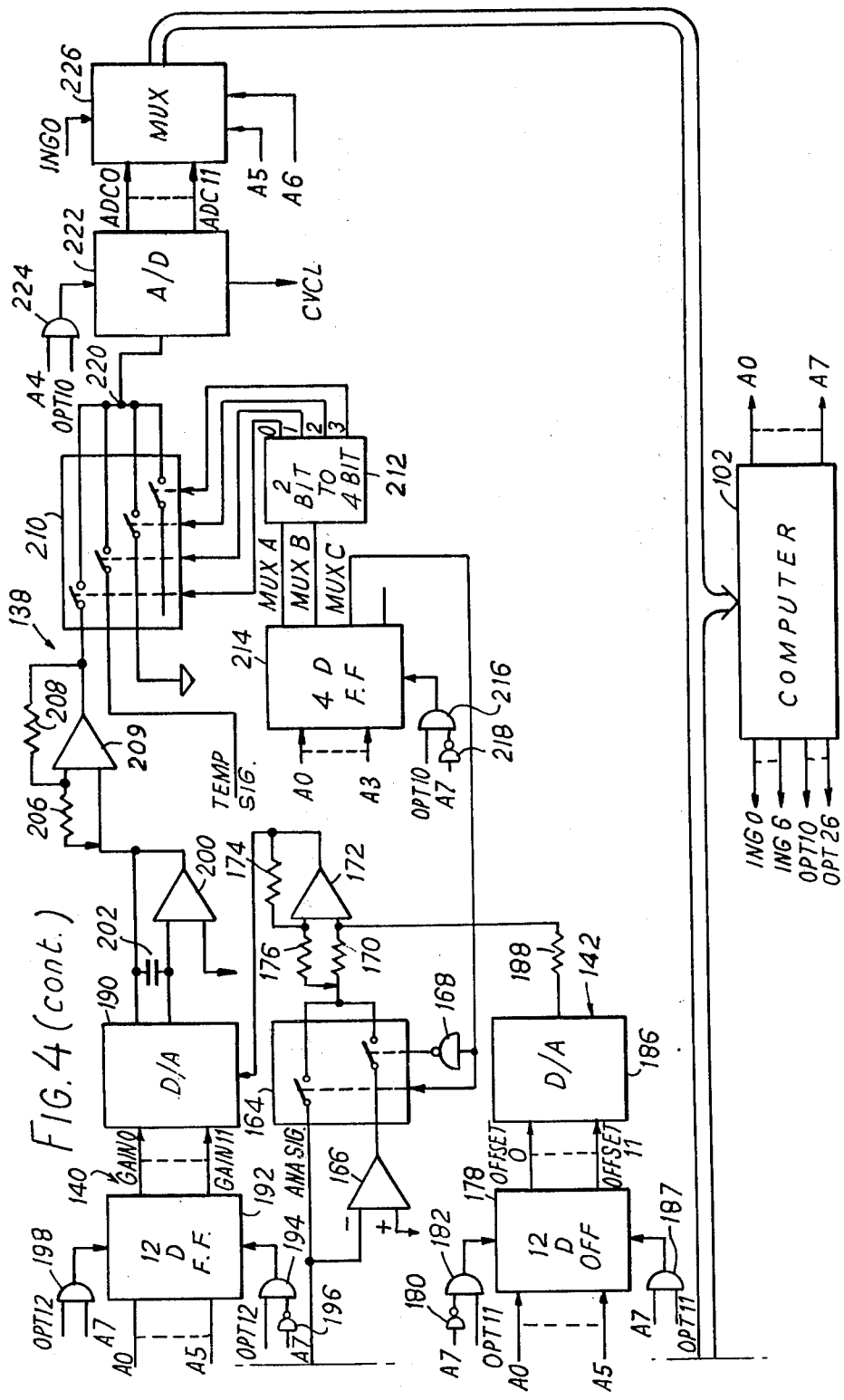

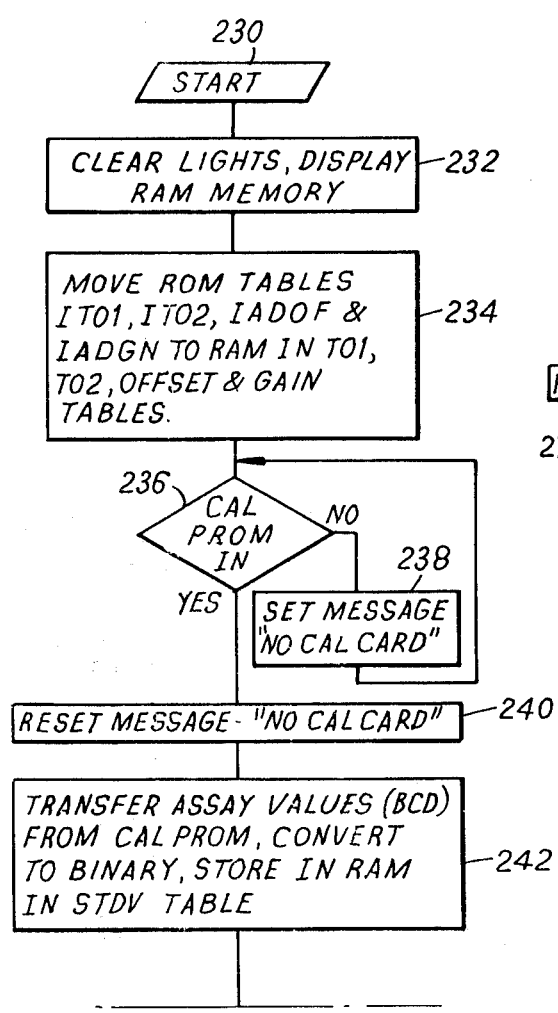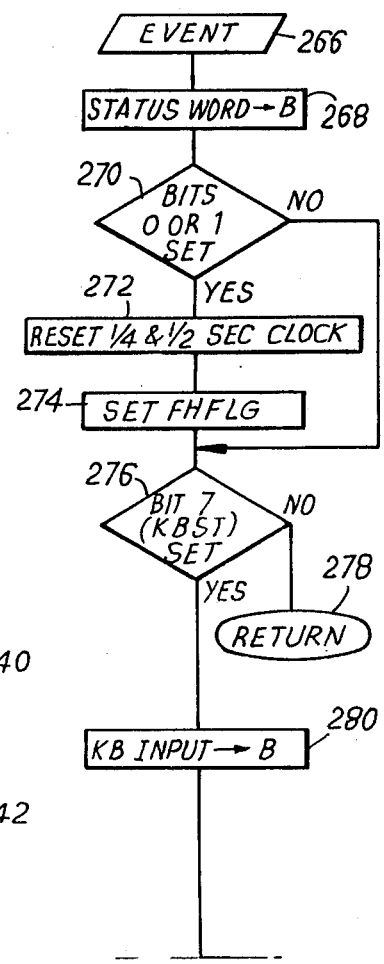

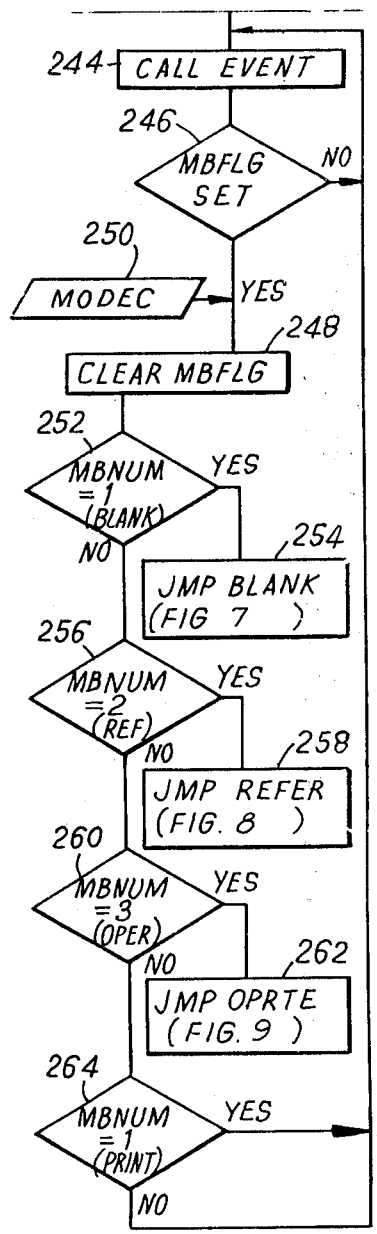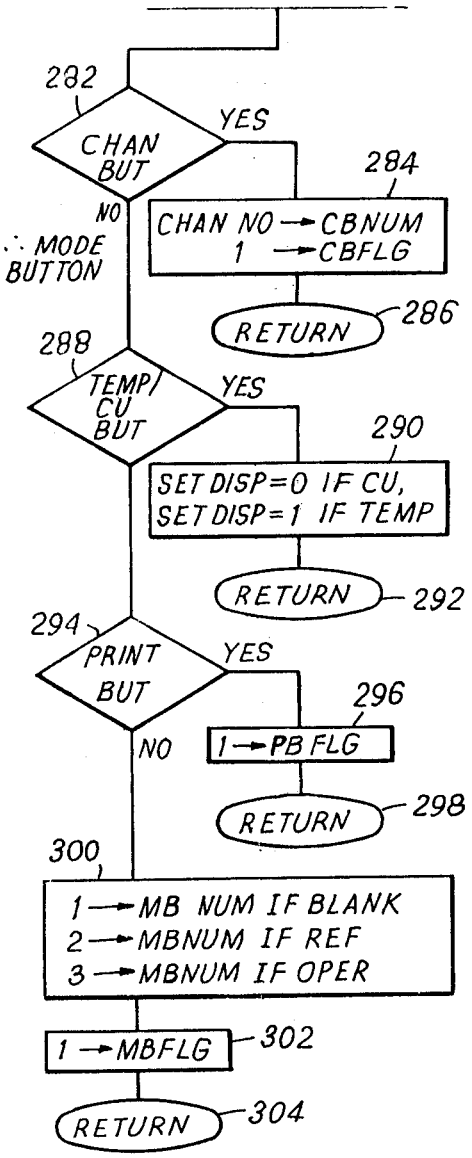

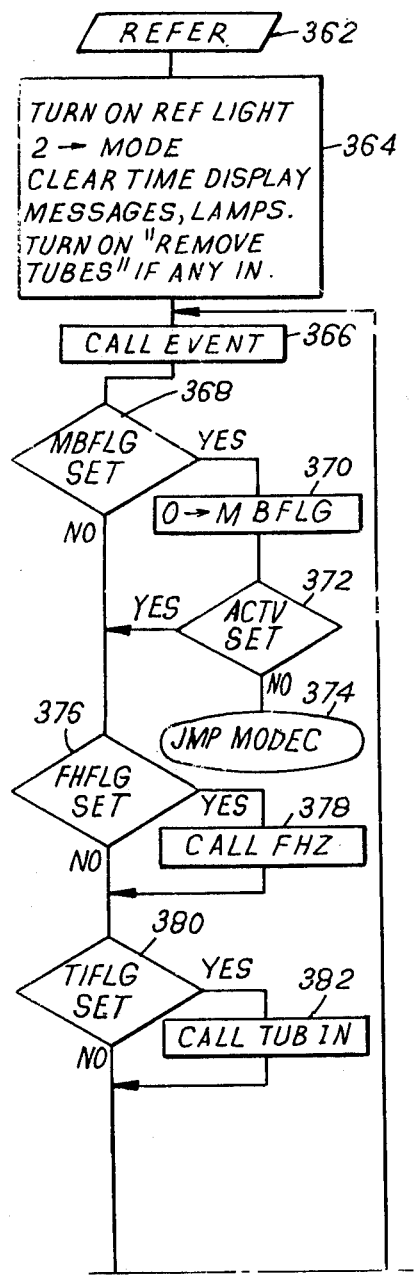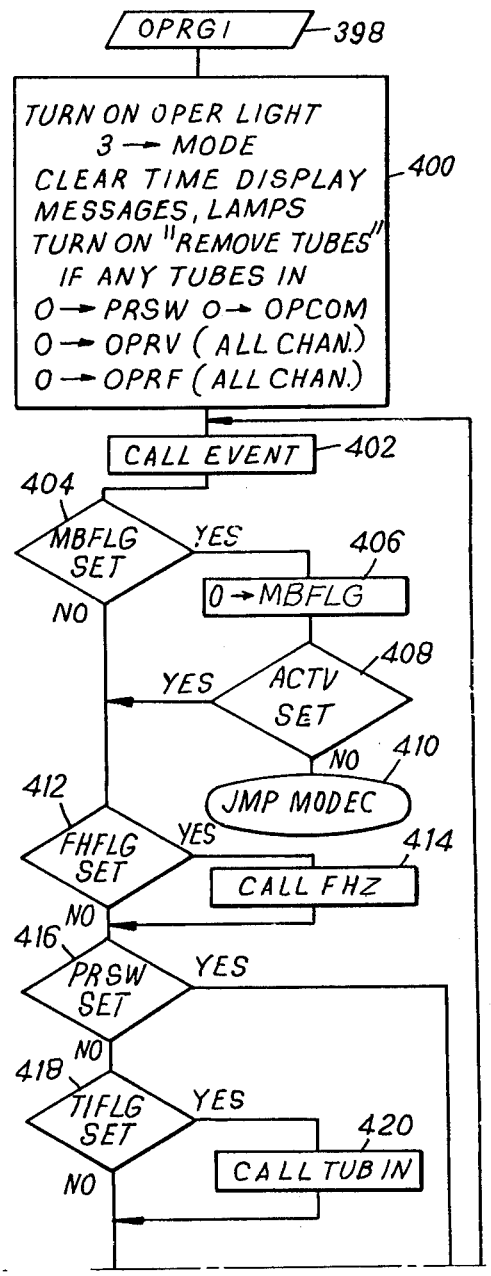

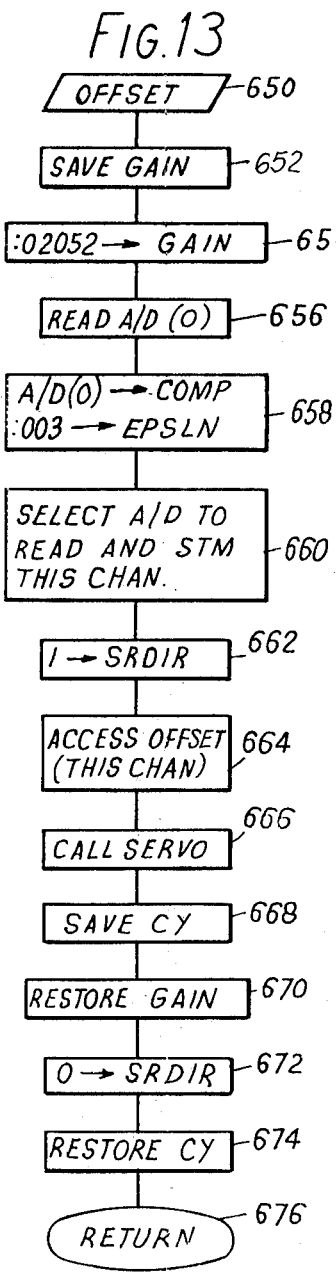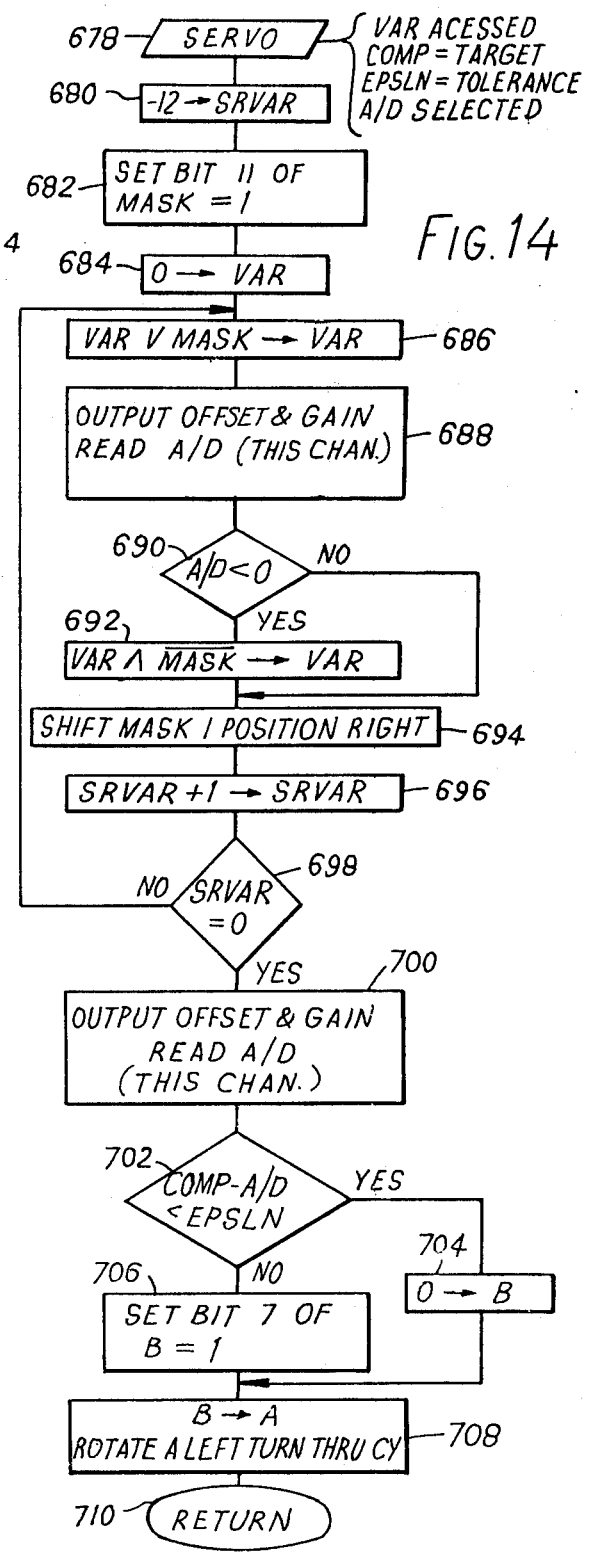

CALIBRATION IN A BLOOD ANALYZER

This invention relates to an automatic chemical analyzer and in particular, to calibration apparatus within such automatic chemical analyzer for minimizing both long term component variations within a single unit and component variations from unti to unit.

In the prior art, an automatic chemical testing system is described in U.S. Pat. No. 3,873,273 in the name of John J. Moran et al which patent is assigned to the present applicant.

In this analyzer, a plurality of substances of blood can be analyzed simultaneously and automatically by mixing pre-designated amounts of blood serum with a chemical reagent designated for the particular substance to be measured. After the mixture is prepared, the container holding the mixture is inserted into a particular dedicated channel of the analyzer for the substance being measured. The analyzer thereafter automatically reads the radiant energy absorbed by the mixture at the proper time or times and calculates the amount of the particular substance being measured and reports such amount in concentration units or in international units, as the case may be, for the particular test.

In order for this analyzer to properly operate, it is first necessary to calibrate the analyzer. This involves a two step process described in the referenced patent as "blanking" and "referencing" the unit. Briefly, blanking involves measuring the voltage provided by radiant energy absorption of the reagent itself and the referencing involves a radiant energy response due to the measuring of the voltage provided by a radiant energy responsive device due to the radiant energy absorption for a known amount of the substance when performing the test. By performing these procedures a scaling factor can be calculated equal to the known value divided by the voltage difference between the obtained blanking and referencing voltage. When the analyzer is then operated with a solution of unknown serum mixed with the chemical reagent, a second voltage difference is obtained equal to the difference between the operating and the blanking voltages. This latter voltage difference can be multiplied by the scaling factor previously determined, and the result in the value of the substance being measured in the desired units.

Prior to making the determinations of the voltage change discussed above in the prior art apparatus, it is necessary to convert the analog voltage provided from the detector to a digital signal. For this single analog-to-digital converter is used and the voltage signals from each of the 16 channels is applied thereto through a multiplexer. As with any analog-to-digital converter, the maximum voltage within which the system operates has its specific limits. For instance, the analog-to-digital converter may only provide output for voltage between minus 10 volts and 0 volts. However with a multichannel analyzer such as the one described in the above referenced patent, various different chemical reactions will provide outputs from the detector associated therewith of varying amounts. Thus the entire sensitivity of the unit must be scaled down to allow the analog-to-digital converter to process each of the chemistries. In other words, in channel 1 a certain chemical reaction will only be allowed to change between 8 and 10 volts whereas in channel 2 a second chemical reaction will only be allowed to change between a$-3$ and $-1$ volts. This is necessary so that the outputs from the detectors associated with each chemical reaction can be applied to the single analog-to-digital converter.

With this scaling down necessitated by the limitations of the analog-to-digital converter, the resolution of the results provided by the analyzer in certain instances may be insufficient to provide precise results. The resolution of the analyzer must further be scaled down in order to accommodate the system for component variations therein. For instance, the xenon lamp radiant energy source, included within the analyzer, must be periodically changed. However, the amount of energy radiated by one lamp will differ from the amount of energy radiated from a second lamp. Further, there are detectors for each channel within the analyzer, and amongst the 16 detectors of prior art analyzer some variation will occur in the response to energy.

Further as the analyzers are mass produced, some variation will occur between units because of the variations of components used within the analyzers. Accordingly, it will be necessary to adjust the components in the analyzers using, for instance, variable resistors which can be adjusted with a screw-driver in a known manner. However this adds both expense to the component costs of the analyzer as well as considerable labor costs in fine tuning the analyzers. Further, by manually fine tuning the analyzers it is difficult to obtain exact results which are desired when measuring substances within blood.

To correct the problems discussed above with regard to the analyzer of the reference Patent, one could use the computer which is included in the analyzer to control its operation to adjust the various component parameters which vary and to adjust the offset voltage provided from each of the detectors to increase the resolution of the value indicated by the analog to digital converter.

In accordance with one aspect of this invention there is provided, in a system in which energy is applied to a detector, means which provide an analog signal responsive to energy. The analog signal is then processed to manifest the energy by which the processed analog signal is effected by element variations from nominal values in the system. The improvement of apparatus for correcting the effect of the variations on the signal includes ratio means, responsive to a first signal applied thereto, and further responsive to a ratio determining signal applied thereto, for providing a signal having a value related to the applied first signal times a ratio determined by the ratio determining signal.

There is also included means for applying the analog signal to the ratio means as the first signal. In addition, there is provided control means for calculating and providing the ratio determining signal while an energy related to a known value is applied to said detector means. The ratio determining signal is calculated to be such that the signal provided by the ratio means has a pre-designated value. The control means then is capable of determining the value related to an unknown energy being applied to the detector means by multiplying the value of the ratio means signal by a factor of the known energy value divided by the predesignated value.

A detailed description of the present invention is hereafter given with specific reference being made to the following figures in which:

FIG. 2 is a perspective view of the block assembly of the analyzer of FIG. 1;

FIG. 3 is a block diagram of the electrical apparatus of the analyzer shown in FIG. 1;

FIG. 4 is a block diagram of the signal processing apparatus shown in FIG1 3; and FIGS. 5 to 14 are flow diagrams of the program within the computer shown in FIGS. 3 and 4 for controlling the operation of the analyzer shown in FIG. 1.

Figure 1:
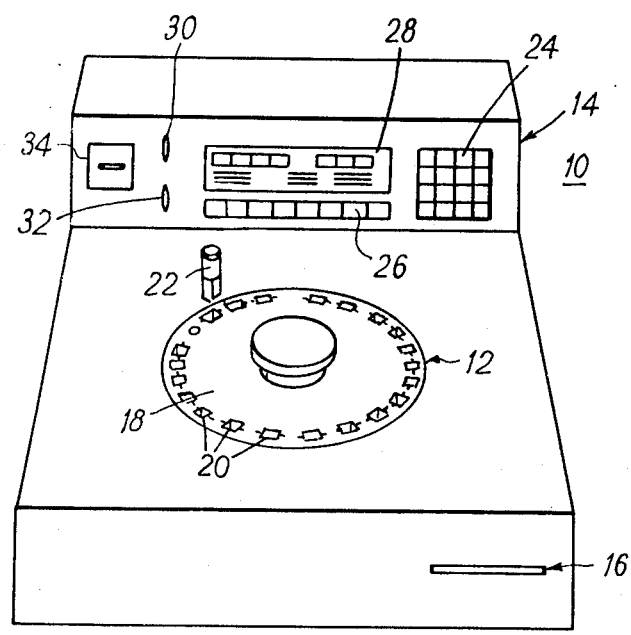
FIG. 1 is a perspective view of the automatic chemical analyzer of the invention.

Referring now to FIG. 1, automatic chemical analyzer 10 is shown and includes a testing area 12, a control area 14 and a printer area 16. Within analyzer 10 is various electronic circuitry, pertinent portions of which circuitry are shown as a block diagram in FIGS. 2 and 3.

Testing areas 12 includes a heating block 18 having a plurality of openings 20 therein, into each of which a container 22 may be inserted.

Container 22 will contain one or more specific chemical reagents mixed in solution with a specific amount of the sample being tested. Upon insertion in an opening 20, the testing procedure begins and a specific time after the insertion of container 22 into opening 20, the radiant energy at a specific wavelength absorbed by container 22 and its contents is detected and an electrical signal having a magnitude proportional to that radiant energy absorption is applied to the electronics within analyzer 10.

Control area 14 includes a plurality of channel buttons 24, which may be illuminated either steadily or in a flashing manner to indicate certain things with regard to a specific test. In addition, a series of mode buttons 26 is provided which may be depressed or illuminated to cause analyzer 10 to enter the blank mode, the calibrate mode, or the operate mode or to print results. In addition, other mode buttons, which are not capable of depression, become illuminated to indicate certain states of analyzer 10 such as it is ready to be placed in the operation mode or that the temperature of heating block 18 is improper.

In addition, area 14 includes a message and data display area 28, which includes a series of messages that may be illuminated to indicate certain instructions to the operator, such as recalibrate. Display area 28 also includes numeric displays upon which the test results or the temperature of heating block 18 may be displayed.

Additionally, area 14 includes a pair of manually settable timers 30 and 32 which may be utilized to set specific times for one of the openings 20 and this function is explained in more detail in the above referred to U.S. Pat. No. 3,873,273.

Lastly, on control area 14 is the calibration card 34 which may be an integrated circuit programmable read-only memory affixed to a printed circuit board. The circuit board includes calibration card 34 and is manually inserted into a circuit-receiving connector so as to be coupled, in circuit, with the system.

Prior to performing an analysis on an unknown substance with analyzer 10, that is the mixing of precise quantities of an unknown substance with different reagents in a plurality of containers 22 and the inserting of each container into the proper opening 20, it is necessary to calibrate analyzer 10, that is to perform an analyis of a sample having known values. A sample having known values of various blood substances desired to be tested by analyzer 10 is known as a control serum or a reference serum. When a test is performed on a known sample, the voltage provided by the detectors reflects the optical density (O.D.) of the test solution. However this is an undesirable unit in which to convey the information to the operator. However, by using the assay value of a known substance a scaling factor equivalent to an assay value divided by an O.D. value can be determined and by multiplying the voltage obtained with unknown samples by the scaling factor, a value in known units can be obtained. Calibration card assembly 34 is used to provide the assay value to the electronics within analyzer 10 and is associated specifically with a particular known control serum utilized. In the event the manufacturer or supplier of the control serum supplies of a different lot number it is necessary to also provide a new calibration card assembly 34, which would contain the assay value of the substances within the new lot of the known sample. These known values would be contained in the read-only memory within the calibration card assembly 34 and the information in the programmable read-only memory would have been placed there by the manufacturer of the known substance.

Referring now to FIG. 2, testing area 12 is shown and includes block 18. Block 18 has a central aluminium-block 36 having openings 20 removed from the periphery thereof. Openings 20 are square holes having a pair of extensions on each side thereof, as more fully explained in U.S. Pat. No. 3,964,867 issued June 22. 1976 entitled "Reaction Container" in the name of John F. Berry. The interior of block 36 is hollow and has an area lower than the surface of the area on which openings 20 are positioned for receiving a cover plate (not shown). The central portion of block 36 is hollow and radiant energy source 38 will be positioned therein in a manner to be hereafter explained. A radiant energy source 38 positioned in an opening 40, which may be a circular opening within the lower portion of block 36, and fits into a connector 42 within opening 40.

Surrounding aluminium block 36 is a sleeve 44 onto which a detector card 46 fits. Sleeve 44 has a circular interior side 48 dimensioned to fit securely against the outer periphery of block 36, thereby closing all four sides of openings 20.

The outer periphery of sleeve 44 consists of a plurality of identical sections 50, each separated by an extension 52. The surface from one extension 52 to the next extension 52 is straight. At the center of each section 50, a cutout portion 54 surrounds the entire sleeve 44. On the upper portion of each section 50, a hole 58 extends through each section 50 and opening 20 and the remainder of block 36 so that a light path exists from radiant energy means 38 out of the hole 58. The insertion of a container 22 within an opening 20 will block the light path through hole 58 and a detector means on a detector assembly 46 will detect a presence or absence of light and thereby manifest a signal indicating the insertion of a container 22 within an opening 20. With portion 54, two holes 60 and 62 extend from the surface of portion 54 to the interior of block 36 sio that a light path exists from radiant energy source 38 through holes 60 and 62. Each hole is positioned to be in alignment with an opening 20 and each hole 62 is positioned to be aligned with the a portion 64 defined between two openings 20. The energy applied through hole 60 will be affected by the radiant energy absorbed by the contents of the reaction container 22 in the container 20, but the energy applied through hole 62 will be unaffected by such contents.

Lower portion 65 of sleeve 44 includes an opening 66 into which another electric component on detector assembly 46 may be inserted in a manner hereinafter described.

Also included within each section 50 or selected sections 50 are holes (not shown) for receiving screws for fixing detector assembly 46 to sleeve 44 and for affixing sleeve 44 to block 36.

A cylindrical member 68 is affixed to the bottom of testing area 12 and affixed to the member 68 is a printed circuit board 70 which may be electrically coupled in circuit with other electrical components of analyzer 10. Board 70 includes a plurality of electrical components affixed thereto which are interconnected to input/output pins (not shown in FIG. 2) by printed wiring on both sides of board 70. The components will include a connector for each of the various channels within the block 18 so that the electrical signals from the detectors on detector assembly 46 can be applied from each assembly 46 to the common board 70.

Referring now to FIG. 3, a block diagram of the electrical system 100 of analyzer 10 is shown. At the heart of the electrical system is a computer 102 which includes a central processing unit (CPU) such as the 8008 integrated circuit assembly manufactured by Intel Corp. of Santa Clara, California, appropriate input/output (I/O) logic and a memory. The memory may include a read-only memory (ROM) and a random access memory (RAM). The ROM will contain a series of computer instructions to be applied to control the CPU to provide signals through the I/O circuitry in a known manner. The RAM memory will be utilized for storing values which are subject to change as the processing continues.

The I/O circuitry within computer 102 will respond to signals from the CPU to communicate output signals from computer 102 and will respond to the input signals applied to computer 102 to communicate with the CPU.

The output signals from computer 102 include the A0 to A7 signals which transmit digital information from computer 102 to the various sub-systems within system 100. In addition, computer 102 provides OPT10 through OPT26 signals, each of which enables a single sub-system or portion thereof within system 100 to respond to the information then present on the A0 through A7 lines. In addition, computer 102 provides the ING0 through ING6 signals to various sub-systems within system 100 to enable those sub-systems to provide information to computer 102 over MD10 through MD17 lines.

Computer 102 is also responsive to signals from clock circuit 104 to control its timing. Clock circuit 104 additionally provides a 4HZ signal to other sub-systems within the system 100.

System 100 also includes test display 106, time display 108, manual switches 110, CAL PROM 112, input logic for the manual switches and the CAL PROM 114, message display 116, mode buttons 118, channel buttons 120 and keyboard coder 122, printer logic 124, printer 126, channels 0 . . . 15 detector logic 128 . . . 130, tube detect logic 132, log ratio circuit 134, channel select logic 136, analog-to-digital converter (ADC) logic 138, gain logic 140, offset logic 142, status logic 144, and a one-fourth and one-half second clock 146.

Test display 106 includes a three digit display having a floating decimal point in which each digit includes a seven segment display of a known type. In addition, test display 106 includes logic responsive to signals applied thereto to control the results to be displayed on the seven segment displays. Test display 106 is responsive to the A0 through A7 signals and the OPT22 and and OPT23 signals from computer 102. Upon application of the OPT22 signal to test display 106, the A0 through A7 signals will contain two binary coded decimal (BCD) digits representing the two least significant digits to be displayed on the seven segment displays. Upon the application of the OPT23 signal to test display 106, the A0 through A7 signals will contain one BCD signal representing the most significant digit to be displayed on the seven segment display and a code indicating at which point the decimal point should be placed for the three digit display.

In addition, test display 106 includes a series of flip-flop circuits for storing the information conveyed by the A0 to A7 signals during the application of the OPT22 and OPT23 signals. The output from each of the flip-flop circuits is applied to three BCD to seven segment converter circuits of a known type; the output from the converter is applied to the seven segment displays. In addition, the outputs from the flip-flops in test display 106 are applied to print logic 124 as the DR00 through DR23 signals to allow print logic 124 to provide signals to printer 126 causing the information displayed to be printed on an output document.

Time display 108 is responsive to the OPT20 and OPT21 signals as well as the A0 through A7 signals from computer 102 and operates in a similar manner to test display 106. However, instead of having a decimal point on the three digit seven segment display in time display 108, a colon appears between the most significant and middle digit of the display.

Manual switches in timers 110 include two manual switches 30 and 32 on control panel 14. Each of the switches provides a four bit BCD signal to input logic 114 as the MT10 to MT13 and MT20 to MT23 signals. CAL PROM 112 is responsive to the A0 to A4 signals from computer 102 and to the RCNA signal from input logic 114. Upon application of the RCNA signal to CAL PROM 112, the A0 to A4 signals address a specific word in the PROM of CAL PROM 112 and that word is provided as the CAL 0 through CAL 7 signals to input logic 114.

Input logic 114 has applied thereto, in addition to the MT10 to MT23 signals and the CAL0 through CAL7 signals, the ING1, A5 and A6 signals from computer 102. Input logic 114 provides a four bit BCD word to the MD10 through MD13 lines and provides an RFRS status signal, which indicates whether CAL PROM 112 is inserted in analyzer 10. The ING1 signal selects input logic 114 to provide signals over the MD10 and MD13 lines and the coding of the A5 and A6 signals determines whether the signal to be provided is that manifesting the signals from manual switches 110 or from CAL PROM 112, and more specifically, which four bits of each of the eight bits from these devices are to be provided.

Message display 116 includes a series of lamps which are capable of illumination. Placed over each lamp is a message to be displayed, and when the lamp is illuminated, the message is displayed. Message display 116 is responsive to the A0 to A3 signals, the OPT25 signal, the A7 signal and the 4HZ signal. The A0 to A3 signals include a code which determines which of the lamps and hence, which of the messages are to be illuminated upon application of the OPT25 signal. Message display 116 also includes a series of flip-flops which store the coded A0 to A3 signals and which are enabled by the A7 signal. The decoding of the A0 to A3 signals occurs upon application of the OPT25 signal. Certain of the messages capable of being displayed by message display 116 are displayed in a flashing manner which flash four times a second. This is controlled by the application of the 4HZ signal to a gate included in the logic of message display 116, which gate is associated with the signals to be flashed.

Mode buttons 118 and channel buttons 120 form a keyboard for entry of command data to analyzer 10. In addition, each of the keys is capable of illumination, which together with the messages displayed on message display 116, inform the operator of any operating problems or to which test the results being displayed by the test display 106 relate. There are seven mode buttons in mode button assembly 118 and these include the blank, reference, operate, print, ready, temperature and power buttons. Depression of each of these bottons causes a signal unique to that button to be applied to keyboard decoder 122.

Channel buttons 120 includes sixteen different channel buttons 24 (FIG. 1) which corresponds to one of the sixteen possible tests performed on the analyzer 10. The depression of any of the channel buttons 24 causes a signal unique to that button to be applied to keyboard decoder 122.

Keyboard decoder 122 in response to the ING3 signal, provides a signal over the MD10 to MD17 lines which manifest the unique code of the signal applied thereto as a result of depressing a button. When a button is first depressed and a signal is applied to keyboard decoder 122, the KBST signal becomes logic "1" to indicate the keyboard status, that is, that a signal has been applied to decoder 122. This status signal will be recognized by status logic 144 in a manner hereafter described.

In addition to performing keyboard functions, mode buttons 118 and channel buttons 120 also are capable of being illuminated. Accordingly, mode buttons logic 118 is enabled by the OPT24 signal to respond to the A3 to A7 signals, which contain a code indicating which button is to be illuminated. In addition, mode buttons logic 118 responds to the A0 signals, which enables flip-flops included therein to be set, and maintain the illumination.

Channel buttons logic 120 is responsive to the A0 to A7 signals as well as the OPT14, OPT15, OPT16, and OPT17 signals and one hz and four hz signals. The OPT14 and OPT15 signals are utilized when it is desired to blink one of the channel buttons, that is, cause it to turn on and off at a one hz rate in response to the one hz signal applied thereto. The OPT14 signal controls channel button 0 to 7 and the OPT15 signal controls channel buttons 8 to 15. The OPT16 and OPT17 signals are applied to channel buttons logic 120 to cause the buttons to flash, that is to turn on and off at a four hz rate in response to the four hz signal applied thereto. In this case the OPT16 signal controls buttons 0 to 7 and the OPT17 signal control buttons 8 to 15. If it is desired that the buttons be continuously on then the OPT14 and OPT16 signals are both applied to cause buttons 0 to 7 to be on and the OPT15 and OPT17 signals are applied to cause buttons 8 to 15 to be on. Channel buttons logic 120 also includes a series of sixteen flip-flops, one for each channel, which responds to the A0 and A7 signals applied thereto, when enabled by the appropriate OPT signal to cause the storage of the signals applied thereto, resulting in the continual blinking, flashing, or constant illumination of the lights beneath the buttons.

Referring now to print logic 124 and printer 126, the DR00 through DR23 signals are applied to print logic 124 as previously mentioned. The DR signals are three BCD signals from time display 106, each of which is applied to a BCD-to-decimal converter circuit within print logic 124 which in turn, provides a single pulse on one of ten lines manifesting the BCD code of the signal applied thereto. Each of the ten outputs from the three BCD-to-decimal converters within print logic 124 is applied to printer 126 to cause the three print wheels within printer 126 to be set to the number manifested by the particular one of each of the three sets of signals provided.

In addition, print logic 124 is responsive to the A0, A1 and OPT13 signals from computer 102. The application of the OPT13 signal and the A0 signal indicate that a test was not performed on the computer, and hence no results should be expected for that test. In this case, the printer wheels are set to print three dashes in the space provided on the form for that test. The application of the OPT13 and A1 signals causes the print solenoid to fire, causing the previously set print wheels to print the number manifesting the test result on the printed form.

In addition, print logic 124 provides a SLIP and PWST status signals. The SLIP signal indicates that the printed form has been inserted in printer 126 and the PWST signal indicates that the three print wheels in printer 126 have been set.

The signal processing logic will now be described. Each of the channels 128 . . . 130 provides three output signals TD___, SIG___, and REF___ where the blank indicates the number corresponding to the particular channel. In addition, each of the channels 128 . . . 130 is responsive to an RL___ signal which causes the read relays included therein to be closed, thereby allowing the SIG___ and REF___ signals to be provided. At any given time, only a single RL___ signal will be provided to the sixteen channels 128 . . . 130 and thus at any given time, only one SIG___ and REF___ signal will be provided. The value of the TD___ signals will be dependent upon whether a tube 22 has been inserted in the opening 20 associated with that particular channel.

Tubes detect logic 132 is responsive to each of the TD0 through TD15 signals from the channels 128 . . . 130. In addition, it is responsive to the ING4 and ING5 signals and provides an eight bit digital word over the MD10 through MD17 lines. Tubes detect logic 132 may be a series of sixteen gates, each having one input coupled to one of the respective TD0 through TD15 signals. The first eight of these gates are responsive to the TD0 through TD7 signals and have a second enable input coupled to the ING4 signal and the second eight gates are responsive to the TD8 through TD15 signals respectively and have a second enable input coupled to the ING5 signal. Upon application of the ING4 or ING5 signals, the particular gates to which they are coupled are enabled, and the TD0 through TD7 signal in the case ING4 is applied, are applied directly to the MD10 through MD17 lines, or in the case of the ING5 is applied, the TD8 through TD15 signals are applied directly to the MD10 through MD17 lines.

Referring now to log ratio circuit 134, each of the SIG signals from channel 0 through 15 128 . . . 130 are coupled together through a common line to one input of log ratio circuit 134. Similarly, each of the REF signals from channels 0 through 15 128 . . . 130 are coupled together and through a common line to a second input of log ratio circuit 134. The output of log ratio circuit 134 is the ANA SIG, which equals the logarithm of the ratio of the SIG to the REF voltage i.e. the logarithm of SIG voltage voltage divided by the REF voltage. The output from log ratio circuit 134 is a negative voltage which may be controlled by amplifiers to be between minus 10 volts and 0 volts.

The particular one of the channels 128 ... 130 applying a SIG and REF signal to log ratio circuit 134 is determined by the signals provided from channel select logic 136. Channel select logic 136 is responsive to the A0 through A3 signals from computer 102 which contain a code manifesting a particular one of the sixteen channels 128 ... 130 to be selected. In addition, channel select logic 136 is responsive to the OPT10 and A7 signals from computer 102 and when both the OPT10 and A7 signals are provided, channel select logic 136 is enabled to respond to the A0 through A3 signals applied thereto. This response includes providing one of the RL0 through RL15 signals as a logic "0" while the remaining ones of the RL0 through RL15 signals are all logic "1". The single logic "0" signal allows the read relay switches within the circuity of that one channels 128 ... 130 to be closed, thereby allowing the SIG and REF signals from that channel to be provided to log ratio circuit 134. Thus since the computer 102 controls which of the RL signals is to be applied, it will inherently know to which one of the channels 128 through 130 the ANA SIG from log ratio circuit 134 pertains.

The ANA SIG signals from log ratio circuit 134 is applied to ADC logic 138 as is an analog ground signal and a temperature signal TEMP from a temperature transducer (not shown) included in block 36. In addition, ADC logic 138 has applied thereto, the OPT10 signal, the ING0 signal, the A0 through A7 signals, twelve gain control signals GAIN 0 through GAIN 11 and twelve offset control signals OFFSET0 through OFFSET11. ADC logic 138 provides signals over the MD10 through MD13 lines and a status signal CVCL indicating that it is completed converting the analog ANA SIG applied thereto into a digital value which may be applied over the MD10 through MD13 lines. The exact operation of ADC logic 138 will be described in detail hereafter with respect to FIG. 4. However, briefly the OPT10 signal in conjunction with the A7 signal determine which of the TEMP, ANA SIG, or analog ground signals is to be converted to a digital value, the particular one being determined by the coding of the A0 through A3 signals. The A4 signal, in conjunction with the OPT10 signal enables the analog-to-digital converter within ADC logic 138 to convert the signal applied thereto to a twelve bit digital value and the ING0 signal in conjunction with the A5 and A6 signals cause the twelve digital bits from the analog-to-digital converter to be applied over the output lines MD10 through MD13, four bits at a time.

Gain logic 140 provides the twelve GAIN 0 through GAIN11 signals in response to the provision of the OPT12 and A7 signals according to the code on the A0 through A5 signals. More specifically when the OPT12 signal is provided with the A7 signal being logic "1", the GAIN 0 through GAIN5 signals are provided in response to the A0 through A5 signals and when the OPT12 signals signal is provided with the A7 signal being logic "0", the GAIN 6 through GAIN 11 signals are provided in response to the A0 through A5 signals. Gain logic 140 may include twelve flip-flop circuits, which are enabled by the OPT12 and A7 or A7 signals to store the value of the A0 through A5 signals at the proper time.

Offset logic 142 is similar to gain logic 140 with the exception that it responds to the OPT11 signal and provides the OFFSET0 through OFFSET11 signals to ADC logic 138. The response of ADC logic 138 to the GAIN and OFFSET signals will be described hereafter with respect to FIG. 4.

Status logic 14A responds to the various status signals KBST, RFRS, PWST, SLIP and CVCL, previously discussed. In addition, status logic 144 is response to the $\frac{1}{2}$ second and $\frac{1}{4}$ second signals from clock 146, which signals are provided every $\frac{1}{2}$ second or $\frac{1}{4}$ second respectively in response to the 4hz signal provided to clock 146. Clock 146 may be two flip-flops coupled as a counter. Status logic 144, in response to the ING6 signal provided thereto, couples the values of the status signals and clock signals applied thereto directly to the MD10 through MD17 lines. Computer 102 may thus determine the status of the various modules within the system by looking at a specific bit of the MD10 through MD17 lines, after sending the ING6 signal to status logic 144.

Referring now to FIG. 4, a detailed description of the signal processing circuits of electrical apparatus 100, shown in FIG. 3, will not be given. Channels 0 through 15, 128 ... 130, each include circuitry identical to that shown for channel 128. This circuit is all included on detector card 46, shown in FIG. 2, and where convenient like-numerical designations are given for elements shown in FIG. 2. The detector circuit 128 for channel 0 128 includes photo-transistor 80 and radiant energy responsive diodes 98 and 96, which may be PIN diodes. Photo-transistor diode 80 is rendered conductive by the application thereto of radiant energy, and when photo-transistor 80 becomes conductive, the collector thereof, which is the TD0 signal becomes close to reference (Ground) voltage. When no radiant energy is applied to the base of photo-transistor 80, the collector and hence the TD0 signal is held at a positive +V voltage by the presence of resistor 150 coupled between the collector and a source of positive voltage +V. Thus, whenever a tube 22 is inserted into one of the openings 20 the light applied to transistor 80 is blocked and transistor 80 becomes non-conductive, thereby causing the TD0 signal to become positive.

The anode of diode 98 is coupled to analog ground and the cathode of diode 98 is coupled to one terminal of a ready relay switch 152. The other terminal of read relay switch 152 is the SIG0 signal. The anode of diode 96 is coupled to analog ground and the cathode of diode 96 is coupled to one terminal of a read relay switch 154. The other terminal of switch 154 is coupled to the REF0 signal.

Both switches 152 and 154 are opened and closed at the same time under the control of a switching circuit 156, which includes an inductor 158 having a diode 160 coupled and parallel therewith. The junction between inductor 158 and the cathode of diode 160 is coupled to a source of positive voltage and to one terminal of capacitor 162, the other terminal of which is coupled to analog ground. The junction between the anode of diode 160 and inductor 158 is coupled to the RL0 signal. When it is desired to close switches 152 and 154, the RL0 signal is set equal to 0 volts from its normal positive voltage level, thereby allowing current to flow from +V source through inductor 158. This creates a magnetic field which closes the relays 152 and 154.

Upon closure of the switches 152 and 154, current in an amount proportional to the amount of radiant energy flows through diodes 96 and 98. With respect to diode 98, the amount of radiant energy is dependent upon the radiant energy absorbed by the contents of the container 22 inserted in the opening of the particular channel, with which the detector circuitry is associated. In the case of diode 96, the amount of current is proportional to the radiant energy applied directly from the source 38.

Each of the RL signals applied to detector circuits 128 . . . 130 are applied from channel select logic 136, which includes a four bit to sixteen bit converter 161 and an AND gate 164. AND gate 164 has two inputs to which are applied the OPT10 signal and the A7 signal respectively. When both of these signals are logic "1", the output of AND gate 164 becomes logic "1" and enables converter 161. When enabled, converter 152 causes one of its sixteen output lines (the RL0 through RL15 signals) to become logic "0" (the others remaining logic "1") in response to the digital code on the A0 through A3 lines.

Each of the TD0 through TD15 signals provided from the transistors 80 in the detector circuits 128 . . . 130 is applied as one input to tubes detect logic 132. Tubes detect logic 132 may include sixteen selectable gates. The first eight of these gates are enabled by the application of the ING4 signal and pass the TD0 through TD7 signals to the MD10 through MD17 lines and the remaining eight gates are enabled by the ING5 signal and provide TD8 through TD15 signals to the MD10 through MD17 lines.

Each of the SIG0 through SIG15 signals provided from diode 98 in detector circuits 128 . . . 130 are coupled at a common point 156 at which appears the SIG signal. Similarly, each of the REF0 through REF15 signals from diode 96 in detector circuits 128 . . . 130 are coupled to a common point 158 at which appears the REF signal. The SIG and REF signals are applied to log ratio circuit 160, which provides a signal as its output thereof equal to the logarithm of the SIG divided by the REF voltages. This signal is applied through a 10 hz filter 162 to eliminate any system or environment noise from the signal provided by log ratio circuit 160. The output from filter 162 is the ANA SIG signal.

The ANA SIG signal is applied directly to one input of multiplexer 164 and through an inverting amplifier 166 to a second input of multiplexer 164. Multiplexer 164 is controlled so that either the ANA SIG signal is applied directly to the output or the output of inverting amplifier 166 is applied directly to the output. The selection is determined by the value of a MUX C signal applied to the control inputs of circuit 164. In the event the MUX C signal is a logic "1", the ANA SIG signal is applied to the output, and in the event the MUX C signal is a logic "0" the output of inverter 168 becomes logic "1", thereby causing output of amplifier 166 to be applied as the output of multiplexer 164. It should be noted that inverting amplifier 166 is adjusted to have unity gain.

The output from multiplexer 164 is applied through resistor 170 to the positive input of an operational amplifier 172. The output of amplifier 172 is connected through a resistor 174 to the negative input of amplifier 172. The junction between negative input of amplifier 172 and resistor 174 is coupled through a resistor 176 to analog ground.

Also coupled to the positive input of amplifier 172 is the output of offset circuit 142, which includes twelve D type flip-flops in a circuit 178. The first six of these flip-flops of circuit 178 are enabled by the application thereto of a logic "0" A7 signal at a time when the OPT11 signal is logic "1". This enabling is accomplished by providing the A7 signal to an inverter 180, the output of which is coupled to one input of an AND gate 182. The other input of AND gate 182 is the OPT11 signal. The output of AND gate 182 is coupled to clock input of each of the first six flip-flops within circuit 178. Coupled to the D input of each of the first six flip-flops in circuit 178 is the respective A0 through A5 signals. The Q output from each of these first six flip-flops is the OFFSET0 through OFFSET5 signals provided from circuit 178.

The second six flip-flops of circuit 178 are enabled by the output of AND gate 184 which has the A7 and OPT11 signals applied to the two inputs thereof. Connected to the D input of each of these six flip-flops is the respective A0 to A5 signals and the Q output of each of these second six flip-flops becomes the OFFSET6 to OFFSET11 signals.

The OFFSET0 to OFFSET11 signals are applied to digital-to-analog converter 186 which converts the value of the twelve bit digital signal applied thereto to an analog signal. This analog signal is then applied through resistor 188 to the positive input of amplifier 172.

At this point it should be noted that the voltage signal at the output of multiplexer 164 has a negative magnitude. The A0 to A5 values applied to offset circuit 152 are selected so that the analog signal applied through resistor 188 is equal to a positive voltage which is added to the negative voltage at the output of multiplexer 164 by amplifier 172.

The output of operational amplifier 172 is applied as the analog reference input to digital-to-analog converter 190 included in ADC logic 140. Digital-to-analog converter 190 has a twelve bit digital input to which are applied GAIN0 through GAIN11 signals. The GAIN0 through GAIN11 are provided from twelve D type flip-flops included in circuit 192. Circuit 192 has associated therewith AND gate 194 and inverter 196. The A7 signal is applied to inverter 196 and the OPT12 signal and the output from inverter 196 are applied to the two inputs of AND gate 194. The output signal from AND gate 194 is applied to the clock inputs to enable six of the flip-flops in circuit 192 to store and provide as the GAIN6 to GAIN11 signals, the digital signal on the A0 to A5 lines applied to the D inputs thereof at the time the OPT12 signal is logic "1" and the A7 signal is logic "0". In addition, circuit 192 has associated therewith AND gate 198 having the OPT12 and A7 signals applied thereto and having its output coupled to the clock input to enable the remaining six flip-flops in circuit 192 to store and provide as the GAIN0 to GAIN5 signals, the digital which have their D inputs coupled signal on the A0 through A5 lines applied to the D inputs thereof at the time the OPT12 and A7 signals are both logic "1". The analog output of digital-to-analog converter 190 is applied to the negative input of operational amplifier 200. The positive input of amplifier 200 is connected to analog ground. The output of amplifier 200 is connected to feedback input of digital-to-analog converter 190. The feedback input and the output of converter 190 are coupled together through a capacitor 202, which is included for noise supression purposes.

The output from amplifier 200 is applied as the positive input of operational amplifier 204. The negative input of amplifier 204 is connected through resistor 206 to analog ground. The output of amplifier 204 is connected through resistor 208 to the negative input thereof. The gain of operational amplifier 204 is controlled by the values of resistors 206 and 208 in a known manner.

The output from amplifier 204 is connected to one input of a four input selectable multiplexer circuit 210. A second input of multiplexer 210 is connected to a temperature signal, TEMP SIG, which is an analog voltage between minus ten and zero volts, depending upon the temperature of block 18. A third input of multiplexer circuit 210 is connected to analog ground and a fourth input is not used. Each of the four inputs of multiplexer 210 are connected through a switch associated therewith to an output which is coupled together at point 220.

Four switches within multiplexer 210 are controlled by the four signals at the output of a two bit binary to four bit digital converter circuit 212, which is responsive to the MUX A and MUX B signals applied thereto. The MUX A, MUX B and MUX C signals are provided from a circuit 214, which includes four D type flip-flops, each of which is enabled by the output of an AND gate 216 which has applied thereto the output of inverters 218 and the OPT10 signal. The A7 signal is applied to inverter 218. The A0 through A3 signals are applied to the D inputs of each of the four flip-flops in circuit 214 and are stored and provided as the MUX A, MUX B and MUX C signals when the OPT10 signal is logic "1" and the A7 signal is logic "0".

Thus, when the A2 signal is logic "1" at the time the OPT10 signal is logic "1" and the A7 signal is logic "0", the MUX C signal becomes logic "1," thereby closing the switch to multiplexer 164 to allow the ANA SIG to pass therethrough. On the other hand, if the A2 signal is logic "0", inverter 168 inverts the MUX C signal and causes the switch in the multiplexer 164 associated with the output of amplifier 166 to close and thereby pass the inverted ANA SIG voltage at the output of circuit 164. When the A0 and A1 signals are both logic "0", the 0 output of circuit 212 becomes logic "1", thereby passing the output of amplifier 204 through multiplexer 210. If the A0 signal is logic "1" and the A1 signal is logic "0", the 1 output from circuit 212 becomes logic "1" and the TEMP SIG is passed through multiplexer 210. If the A0 signal is logic "0" and the A1 signal is logic "1", the 2 output from circuit 212 becomes logic "1" and the analog ground signal is passed from multiplexer 210.

The four outputs of multiplexer 210 are coupled together at common point 220 which is applied as the analog input to analog-to-digital converter circuit 222. Analog-to-digital converter circuit 222 converts the analog signal applied thereto to a twelve-bit digital signal ADC0 through ADC11 upon the application of the enabling signal at the output of the AND gate 224. AND gate 224 has applied to its two inputs the A4 signal and the OPT10 signal. After the conversion is completed, analog-to-digital converter circuit 222 provides CVCL status signal.

ADC0 through ADC11 signals from analog-to-digital converter 222 are applied to multiplexer 226, which in response to the ING0 signal and the code of the A5 and A6 signals, provides four bits at a time to the MD10 through MD13 lines. When both the A5 and A6 signals are logic "0", the ADC0 through ADC3 signals are provided from multiplexer 226; when the A5 signal is logic "1" and the A6 signal is logic "0", the ADC4 though ADC7 signals are provided from multiplexer 226; and when the A6 signal is logic "1" and the A5 signal is logic "0" and the ADC8 through ADC11 signals are provided from multiplexer 226.

Thus, with the circuitry shown in FIG. 4, the analog signals provided from the diodes 96 and 98 in each of the channel 0 and channel 15 circuits 128 . . . 130 can be provided to computer 102 as a digital signal properly adjusted for offset and gain.

Referring now to FIG. 5, a flow diagram of the computer program controlling computer 102 immediately after the application of power will now be described. START program 230 includes blocks 232 and 234. According to block 232, immediately after the application of power to computer 202, all of the lights, displays and the RAM memory are cleared. Then, according to block 234, certain information in ROM memory tables is moved to RAM memory tables. This information includes the ITO1 and ITO2 tables, which contain the times at which the various channels are to be read. The ITO1 and ITO2 tables are transferred to the TO1 and TO2 tables in the RAM memory. Further the ROM tables include the IADOF and IADGN tables which include initial offset and gain values which are moved to the OFFSET and GAIN tables in the RAM.

The ROM table is hereafter set out as Table 1 for channels 0 though 15.

Table i

| CHAN NO. | ITO1 | ITO2 | IADOF | IADGN | ULIM | LINEAR | OFADJ | CLBR | TYPE | DCPT | INVRS |
|---|---|---|---|---|---|---|---|---|---|---|---|
| 0 | 0 | 5 min. | 0 | HO-/OOOB | 17/240B | 004B | 0 | 12 B | 1 | 0 | 0 |
| 1 | 0 | 7 min. | 0 | | | | 0 | 13 B | 1 | 1 | 0 |
| 2 | 0 | 4 min. | 0 | | | | 0 | 13 B | 1 | 1 | 0 |
| 3 | 2 sec | 7 min. | 0 | | | | 10/000B | 13 B | 4 | 1 | 4 |
| 4 | 0 | 3 min. | 0 | | | | 0 | 12 B | 1 | 1 | 0 |
| 5 | 2 sec | 7 min. | 0 | | | | 10/000B | 13 B | 4 | 1 | 0 |
| 6 | 0 | 2 min. | 0 | | | | 0 | 13 B | 1 | 1 | 0 |
| 7 | 2 sec | 7 min. | 0 | | | | 2/000B | 11 B | 4 | 1 | 0 |
| 8 | 30 sec | 90 sec | 0 | | | | 10/000B | 13 B | 4 | 1 | 4 |
| 9 | 0 | 5 min. | 0 | | | | 0 | 13 B | 1 | 0 | 0 |
| 10 | 2 min | 7 min. | 0 | | | | 0 | 12 B | 2 | 0 | 0 |
| 11 | 2 min | 7 min. | 0 | | | | 0 | 13 B | 2 | 0 | 0 |
| 12 | 2 min | 7 min. | 0 | | | | 0 | 13 B | 2 | 0 | 4 |
| 13 | 2 min | 7 min. | 0 | | | | 0 | 13 B | 2 | 0 | 4 |
| 14 | 2 min | 7 min. | 0 | | | | 0 | 12 B | 2 | 0 | 0 |
| 15 | 0 | 0 | 0 | | | | 0 | 13 B | 8 | 3 | 0 |

In addition to the ITO1, ITO2, IADOF and IADGN tables, there are also the ULIM, the LINEAR, OFADJ, CLBR, TYPE, DCPT and INVRS tables. The ULIM and LINEAR values are utilized as constants to determine whether the information is proper in the manner explained thereafter. The OFADJ and CLBR tables are utilized to obtain target values during the calibrate mode of operation. The TYPE table indicates the type of reaction which is occurring in the particular channel. The code of the TYPE is that a type 1 reaction is an "end point" reaction, that is, the radiant energy absorbed by the contents of the tubes 22 is measured at a specific time determined by the value in the ITO2 table. A type 2 reaction is a "rate" reaction, that is the radiant energy absorption of the contents of tube 22 is measured at 3 points in time, the first one of which is stored in the ITO1 table and the third one of which is stored in the ITO2 table and the middle one of which is equal to one half the value stored in the ITO2 table. A type 4 reaction is a "special rate" reaction, that is, two readings are taken of the radiant energy absorbed by the contents of the tube 22 in those channels, and these readings are taken at times set out in the ITO1 and ITO2 tables respectively. To calibrate the different types of reaction, different methods are used. In the case of an end point reaction, it is necessary to blank and reference the analyzer. The blanking occurs by inserting in the opening 20 a tube 22 having only reagent therein with no serum added. To reference the analyzer for an end point reaction, it is necessary to perform a test using a serum having a known assay value of a particular substance being tested. To calibrate a special rate reaction, blanking is not necessary. The referencing is the same as the referencing for an end point reaction.

To calibrate for a rate reaction, it is necessary to both blank and reference. However, instead of using reagents and known serums, calibrating elements having interference filters of a specific wavelength which absorb radiant energy in a known manner are utilized. There are two such elements provided with analyzer 10. One for blanking in which a certain amount of energy is absorbed by the blanking element and one for referencing in which a second certain amount of energy is absorbed by the referencing element. It should be noted that the same blank element and reference element may be used for each rate reaction channel.

The final type of reaction is a manual reaction, which is designated as a type 8 reaction, for which special processing involving determining the times from the manual timers is necessary.

The DCPT column in Table 1 indicates the place in which the decimal point should occur in the print out and display. As can be seen, this is either before or after the first digit with the exception of the manual channel, in which case it is before the most significant digit.

The final column in Table 1 is labeled INVRS and contains a "4" for those channels in which a reaction is inverse to the normal, that is, in which a reaction goes from a more intense color to a less intense color. For the channels having the "4" for the INVRS table, the MUX C signal becomes logic "0", thereby causing ANA SIG signal to be inverted by amplifier 166 and applied through multiplexer 164; for those channels having a "0" in the INVRS column, the ANA SIG signal is applied directly through multiplexer 164.

Continuing with FIG. 5, after the ROM tables are moved to the RAM, block 236 indicates that a determination is made whether the CAL PROM 112 has been inserted. This may be accomplished by computer 102 providing an ING 6 signal and then determining the value of the RFRS signal applied over the MD10 through MD17 lines. If the RFRS signal is logic "1", the CAL PROM 112 has been inserted and if the RFRS signal is logic "0", the CAL PROM has not been inserted. If the CAL PROM 112 has not been inserted, then according to block 238, computer 102 sends out signals to cause the message "NO CAL CARD" to be displayed on message display 116. This can occur, for instance, by the computer 102 sending out a code in the A0 through A3 signals relating to the lamp beneath the NO CAL CARD message while logic "1" the OPT12 and A7 signals are provided.

Assuming at block 236 it is determined that the CAL PROM 112 has been inserted, then block 240 indicates that the message NO CAL CARD is reset in message display 116. This may be done by applying the A0 through A3 code to the message NO CAL CARD while the OPT25 signal is logic "1" and the A7 signal is logic "0".

Next, according to block 242, the values in the CAL PROM are transferred to computer 102, converted from the BCD values stored in the RAM memory and the STDV table thereof. This transfer may occur by providing the ING1 signal with the proper coding on the A5 and A6 lines to cause input logic 114 to provide the CAL0 through CAL7 signals four bits at a time from CAL PROM 112. The ING1 signal becomes the RCNA signal and at the time of its provision, the A0 through A4 signals address the desired word from CAL PROM 112. Conversion and storage are done within computer 102 in a known manner.

Next, according to block 244, EVENT program 266 is executed. EVENT program 266 is shown in FIG. 6 and will be explained in detail when FIG. 6 is described. Briefly, however, EVENT program 266 sets the FHFLG word in RAM memory each time the ¼ second clock 146 provides a signal. In addition, EVENT program 266 checks whether keyboard decoder 122 has had applied thereto a keyboard signal from either the mode buttons or the channel buttons, and in the event it has certain flags set and certain values are stored in other locations of the RAM memory. Specifically, in the event a mode button is depressed, the MBFLG word in the RAM memory is set to logic "1" and a value equal to 1, 2 or 3 is transferred to the MBNUM location to indicate the BLANK, REFERENCE or OPERATE buttons were respectively depressed. In the event the PRINT button is depressed, the PBFLG word is set equal to logic "1". If one of the channel buttons 120 is depressed, the CBFLG word is set equal to logic "1" and the number of the particular channel button is stored in the location CBNUM.

Next, according to block 246, a determination is made of whether the MBFLG word had been set during execution of the EVENT program 266. If the MBFLG word had not been set, thereby indicating no mode buttons had been depressed, a return to block 244 occurs and the EVENT program 266 is again executed. This routine continues until such time as one of the mode buttons is depressed and the MBFLG word is set. Once the MBFLG word is set and the determination at block 246 is positive, block 248 indicates that the MBFLG word is cleared.

It should be noted at this point that a return point MODEC 250 occurs between blocks 246 and 248.

Next, according to block 250, a determination is made whether the MBNUM word is equal to "1", indicating that the BLANK button had been depressed. If MBNUM equals "1", then according to block 254, a jump to BLANK program 306 in FIG. 7 occurs. If the MBNUM word is not equal to "1", then according to block 256 a determination is made whether it is equal to "2", thereby indicating the REFERENCE button had been depressed. If the MBNUM word equals "2", then according to block 258 a jump to the REFER program 362, shown in FIG. 8, occurs. If MBNUM does not equal "2" then block 260 indicates a determination is made whether MBNUM equals "3" thereby indicating the OPERATE button had been depressed. If MBNUM equals "3" then block 262 indicates a jump to OPRTE program 398, shown in FIG. 9, occurs. If the MBNUM does not equal "3" at block 260 then according to block 264, determination is made whether MBNUM equals "4", thereby indicating that the PRINT button had been depressed. Whether or not the PRINT button had been depressed at block 264, a return to block 244 occurs, because at this point there is nothing to be printed and in any event, as will be seen hereafter, a depression of the PRINT button results in a call of PRINT routine during the execution of the BLANK, REFER or OPRTE programs, rather than a jump to a PRINT program directly.

Before, describing in detail, the BLANK, REFER or OPRTE programs, which are jumped to at blocks 254, 258 or 262 respectively, referece is made to FIG. 6 for a description of EVENT program 266 which consists of blocks 268 through 304. First according to block 268, the status word is checked and stored in the B register of computer 102. This may occur by computer 102 providing the ING6 signal, and in response thereto the status word appears on the MD10 through MD17 lines from status logic 144. Then, according to block 270, bits "0" and "1" thereof are checked to determine if they are logic "1". As previously discussed bits "0" and "1" carry the respective status from the ¼ and ½ second clock 146. If either have been set, then according to block 272, clock 146 is reset. This may occur by providing the OPT 26 with the A0 signal equal to logic "0". Next according to block 274, the FHFLG location in the RAM memory of computer 102 is set equal to "1". If at block 270 it had been determined that bits 0 or 1 of the status word had not been equal to logic "1", then blocks 272 and 274 are skipped.

Continuing with block 276, bit 7 of the status word is checked to determine whether the keyboard status signal KBST is equal to logic "1", thereby indicating that a mode button 118 or a channel button 120 had been depressed. If bit 7 of the status word is equal to logic "0", then block 278 indicates a return to the calling program occurs.

If at block 276 it is determined that bit 7 is logic "1", then block 280 indicates that the keyboard input is transferred to the B register of computer 102. This may occur by providing the ING3 signal to circuit 122, thereby causing the MD10 through MD17 signals to convey a code indicating which button of the mode buttons 118 or channel buttons 120 had been depressed.

Next, block 282 determines whether the code in the B register indicates a channel button had been depressed. If it had, block 284 indicates that the channel number is stored in the location CBNUM and CBFLG is set equal to "1" and block 286 indicates a return to the calling program occurs. If the decoding indicates a channel button has not been depressed, then block 288 indicates a determination is made whether the temperature or CU button had been depressed. If it had, then according to block 290 the value in location DISP is set equal to "1" if the TEMP button had been depressed.

If the TEMP and CU buttons had not been depressed, then according to block 294, a determination is made whether the PRINT button has been depressed. If it had, then block 298 indicates that a return to the calling program occurs.

If at block 294 it had been determined that the PRINT button had not been depressed then by the process of elimination, one of either the MODE, REFER or OPRTE buttons had been depressed. Thus, according to block 300, if the BLANK button had been depressed, a "1" is stored in the MBNUM location; if the REFER button had been depressed a "2" is stored in the MBNUM location; and if the OPERATE button had been depressed, a "3" is stored in the MBNUM location. Then, according to block 302, a "1" is stored in the MBFLG location and according to block 304 a return to the calling program occurs.

Figure 7:
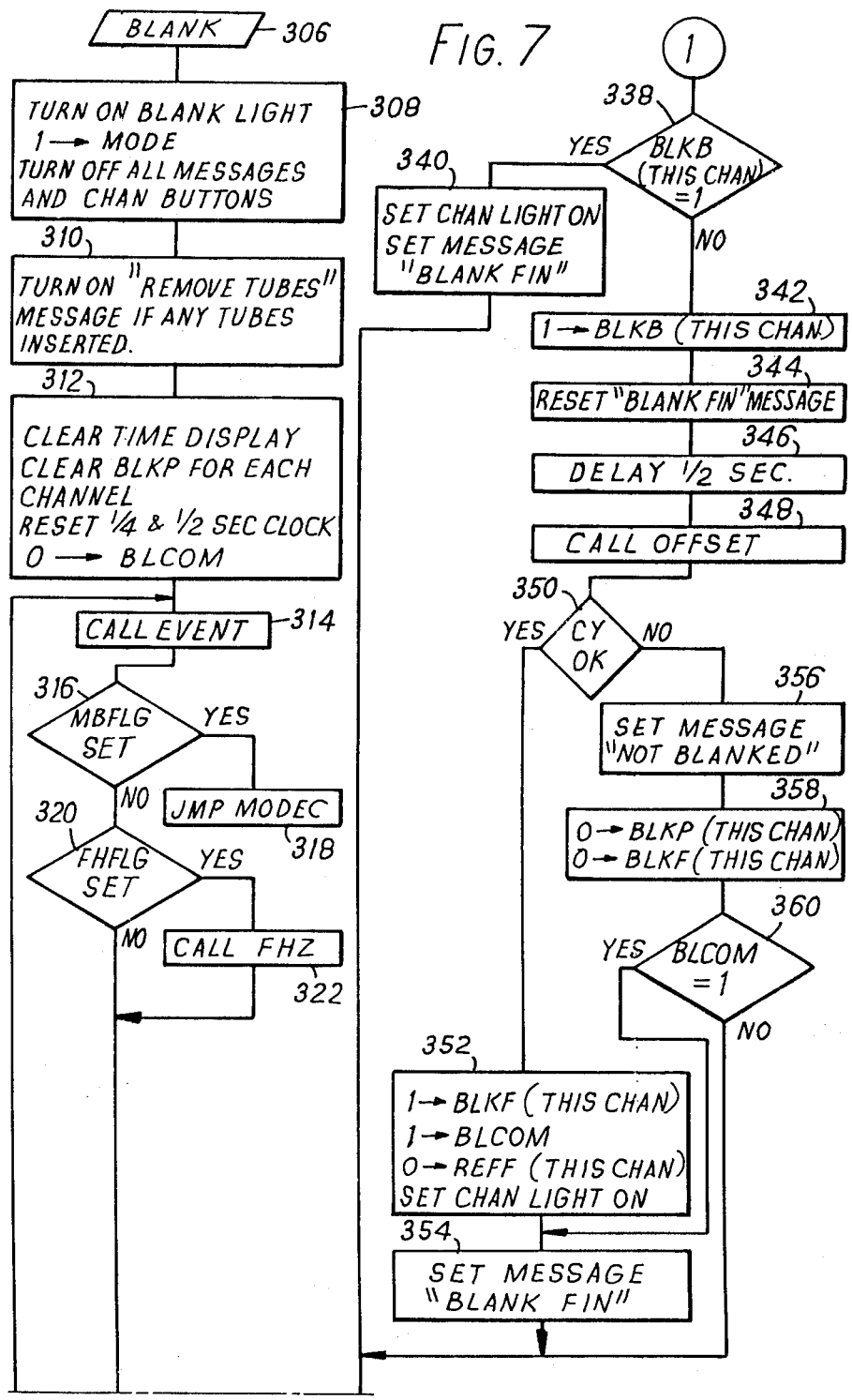
Figure 7:
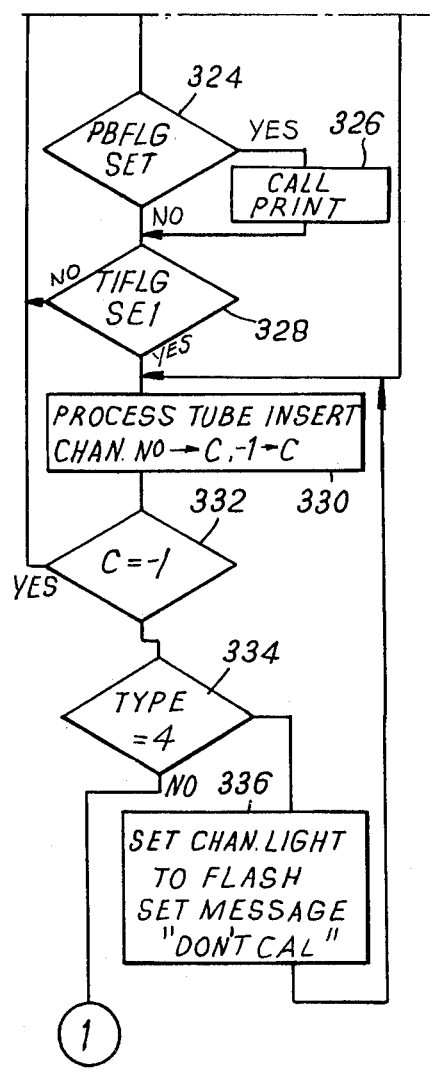

If at block 252 in FIG. 5, a determination had been made that a "1" is stored in the MBNUM location, indicating the BLANK button had been depressed, then block 254 indicates a jump to BLANK program 306 in FIG. 7 occurs. Referring now to BLANK program 306 in FIG. 7, it includes blocks 308 through 360.

According to block 308, as soon as a jump occurs to BLANK program 306, the light beneath the BLANK mode button is turned on and a "1" is transferred to the MODE location to indicate that the BLANK program is being executed. Then all of the other messages and channel button lights are turned off by applying the proper signal to circuits 116 and 120 in the manner previously described.

Next according to block 310, the REMOVE TUBES message is turned on if any tubes 22 remain in any of the holes 20 and this message remains on until the tubes are removed.

Next, according to block 312, time display 108 is set to display a time of zero and the BLKP tables in the RAM, which has one location for each of the channels, is cleared. Further clock 146 is reset to synchronize it with BLANK program 306. Finally according to block 312, the BLCOM location is reset to "0".

Next according to block 314, EVENT program 266 is called for execution and the FHFLG is set in the event the ¼ second clock is set by the 4 hz signal. Further, during the execution of EVENT program 266, if one of the mode buttons has been depressed, then the CBFLG, PBFLG or MBFLG locations are set equal to "1", depending upon which mode button has been depressed in the manner previously explained.

Continuing with block 316, the first determination is whether the MBFLG location had been set. If set, a jump to the MODEC return point 250 in FIG. 5 occurs and a jump to a BLANK, REFER or OPRTE program occurs as indicated at blocks 254, 258 and 262 thereof.

Figure 10:
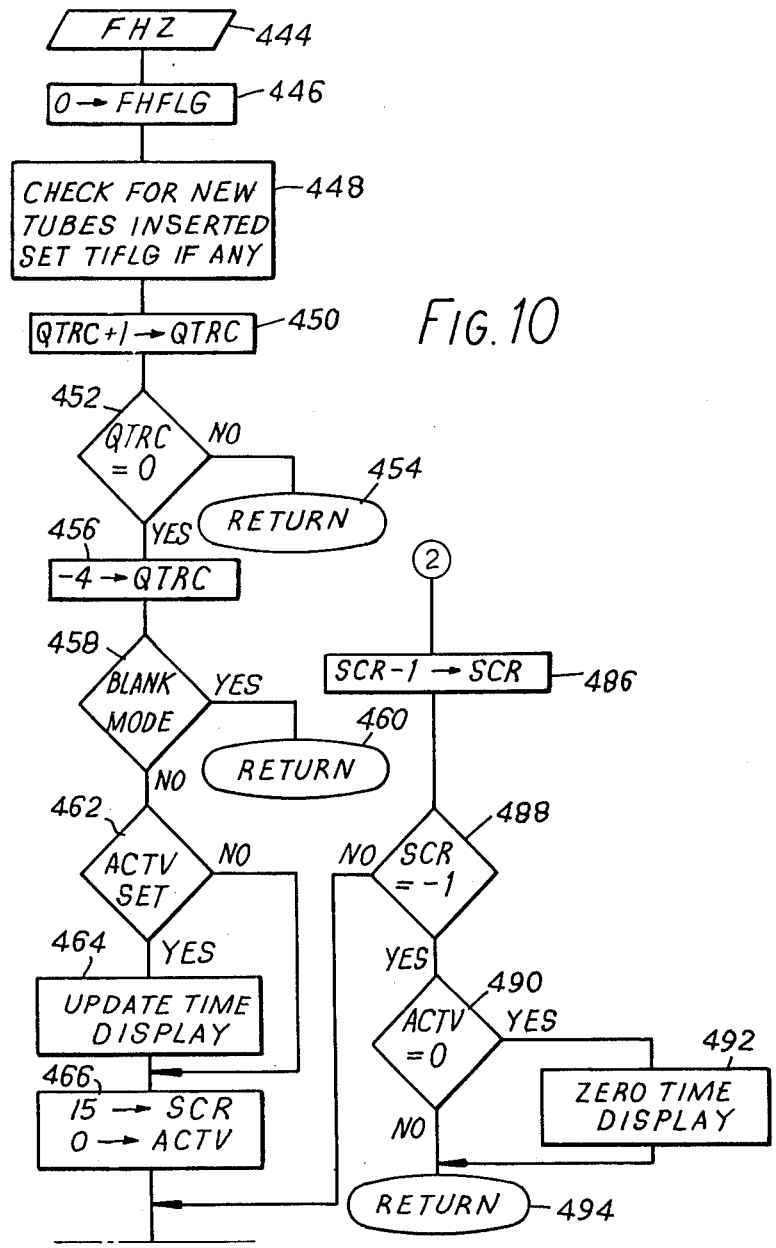
Figure 10:
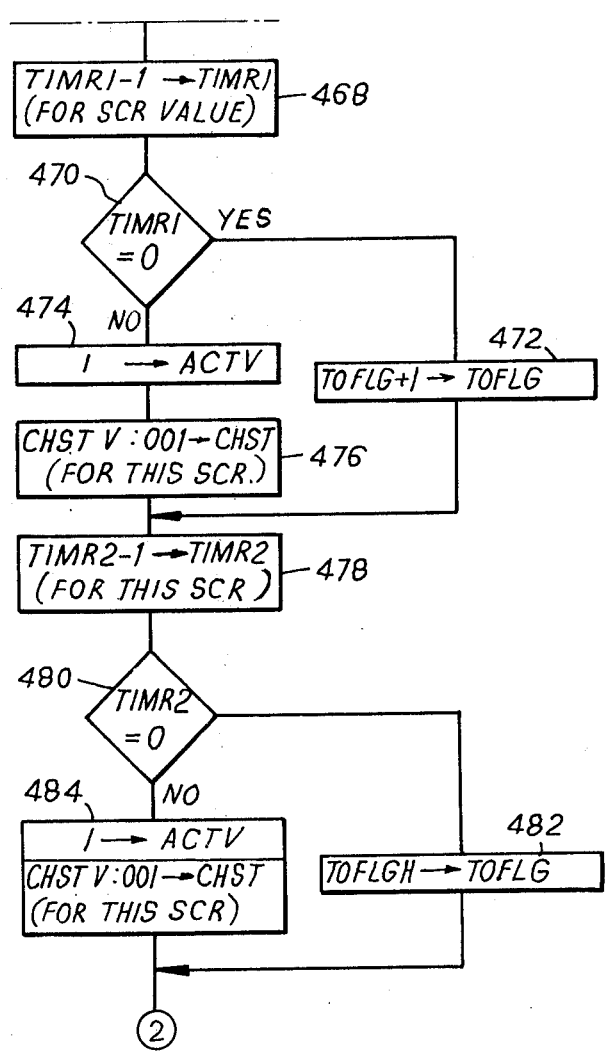

If the MBFLG is not set, then according to block 320, determination is made whether the FHFLG flag is set. If it is, the FHZ program 444, shown in FIG. 10, is called for execution as indicated by block 322. During execution of the FHZ program 444, a determination is made whether any new tubes have been inserted and if they have the TIFLG is set. Further, during the FHZ program 444, an internal counter is set equal to minus 4 and incremented each time the FHZ program is called, which occurs once every 250 milliseconds. Thus, the internal counter becomes zero after one second and upon the occurrence of this, each of the timers, such as the TIME OUT timers and the clock display, are updated by one second. Then, a determination is made whether the timeout 1 or timeout 2 counters are equal to 0 and in the event they are, the TOFLG location is set. This determination of the timeout counters occurs for each channel which had been rendered active by the insertion of a tube. Thus, a TOFLG location is incremented by one each time a timeout detection occurs. Further, as long as the second timeout counter is non-zero, the ACTV FLG is maintained in a set state.

If the FHFLG flag is determined not to be set at block 320, then according to block 324, a determination is made whether a PBFLG is set. If set, the PRINT routine is called for execution as indicated by block 326. During this routine, the information stored in the location OPRV for each channel is printed as will be discussed hereafter with respect to FIG. 12B. This information is the result of the analysis performed on each of the active channels.

If the PBFLG is not set, then according to block 328 a determination is made whether the TIFLG flag had been set during the execution of the FHZ program. If the TIFLG is not set, then a return to block 314 occurs and the procedure from blocks 314 through 328 is repeated.

However, if it is determined that the TIFLG has been set, then according to block 330 the new tube inserted is processed by causing the channel number for that inserted tube to be stored in the C register of computer 102. If no tube is determined to be inserted at this point, or is determined to have been removed, then a minus one is placed in the C register of computer 102. Then, as indicated by block 332, a determination is made whether the C register is equal to minus one. If it is, a return to block 314 occurs.

Assuming that a channel number is present in the C register, then a determination is made whether the reaction is a type four or a special rate reaction as indicated by block 334. It if is, the message DON'T CAL is turned on by applying the appropriate signals to message display 116 from computer 102. As previously mentioned it is not necessary to blank the special rate reaction.

However, if the type of reaction is other than special rate reaction a determination is made whether the BLKB location for this channel has been set as indicated at block 338. The BLKB table includes one word for each channel of analyzer 10 and this word is set whenever that channel has been blanked. Thus, if it is determined at block 338 that the BLKB location for this channel had been set, then according to block 340, computer 102 sends the proper signals to message display 116 to cause the BLANK FIN, or blank finished, message to be illuminated. Thereafter, a return to block 330 is indicated and the tube insert processing again occurs and the channel number or minus one is stored in the C register.

If at block 338 it had been determined that the BLKB location had not been set, that is that particular channel had not been blanked, then according to block 342 the BLKB location for that channel is set so that it will not again be blanked. Then according to block 344, the BLANK FIN message is reset if it had been set at block 340 during the previous loop within BLANK program 306.

Then, according to block 346, a delay of one-half second occurs to allow the contents of the just inserted tube to settle and all air bubbles float to the top and dissipate. Next, according to block 348 OFFSET program 650, shown in FIG. 13, is called for execution. During the execution of OFFSET program 650, the offset signals from offset logic circuit 142 are determined. This occurs by initially setting each of the offset signals at zero, while the analog to ground input to multiplexer 210 in FIG. 4 is connected to analog-to-digital converter 222. Then, beginning with the most significant bit of the offset signals, they are turned on one at a time and a determination is made whether the digital output from converter 222 is less than zero volts. If it is, the just turned on bit is turned off, if not, it is left on. Then, the next most significant offset signal bit is turned on and a determination is made whether the output from converter 222 is less than zero volts. If not, the second most significant bit is left on; otherwise it is turned off. This continues until each of the twelve offset signal bits have been checked and the output from converter 222 should at this time be very close to zero volts. During this checking of the offset bits, an artificial gain value, which had been previously determined from other circuit parameters experimentally, is used as the GAIN 0 through GAIN 11 signals. This gain may be a binary number 001000101010. The digital results of the offset value, as determined for this channel, is then stored in an OFFSET location in the RAM memory, and each time thereafter that this channel is to have its signals processed, that offset word value will be utilized.

After the determination of the offset signal values, but during the OFFSET program 650, a check is made to determine whether the signal processed with the determined offset values is within certain limits of zero volts. If it is not, a carry register in computer 102 is set, otherwise, it is left unset.

Upon return from the execution of the OFFSET program 650, block 350 indicates a determination of the carry register in computer 102 is made. If it is determined not to be set, then block 352 indicates that the BLKF flag for this channel is set and a "1" is stored in the BLCOM location. Further, an "0" is stored in the REFF flag for this channel to indicate that this channel must now be referenced. Then, a channel latch controlling the light under the channel buttons for the channel just processed is set thereby turning the light is on. Next according to block 354, the message BLANK FIN is illuminated and thereafter a return to block 330 occurs to process any further inserted tubes.

If at block 350 the determination has been made that the carry location was set, indicating that the offsetting procedures was insufficient, then according to block 356, the message NOT BLANKED is caused to be illuminated on message display 116 then, according to block 358, a "0" is stored in the BLKP and BLKF locations for the particular channel to indicate that that channel has not been blanked. Thereafter, a determination is made at block 360 whether the BLCOM location is equal to one. If it is, a return to block 354 occurs and the message BLANK FIN is illuminated to indicate that other channels having channel lights on have been blanked. It should be noted that at block 354, the message had been turned off. If the determination at block 360 is that the BLCOM location is not equal to 1, then a return to block 330 occurs and a new tube insertion is determined and processed.

In summary, during the blanking operation, each channel of an end point, rate, or manual reaction (type 1, type 2, or type 8), have either a container of reagent with no serum inserted in the opening with which that reagent is associated in the case of the end point reactions or having calibration elements for blanking inserted in the openings in the case of the rate reaction and mannual channels. The blanking results in the offset signal from circuit 142 being determined and provided to offset the voltage provided to the digital-to-analog converter 190 in circuit 140.

It should be noted that BLANK program 306 is a continuous loop through block 314 which calls the EVENT program 266. The manner by which an exit from BLANK program 306 can occur is when the MBFLG location is set during EVENT program 266 as a result of the depression of the reference or operate mode buttons and a jump to MODEC routine 250 occurs, as indicated in block 318. From MODEC routine 250, a jump to the REFER or OPRTE programs 362 and 398 shown in FIGS. 8 and 9 respectively can then occur.

Figure 8:
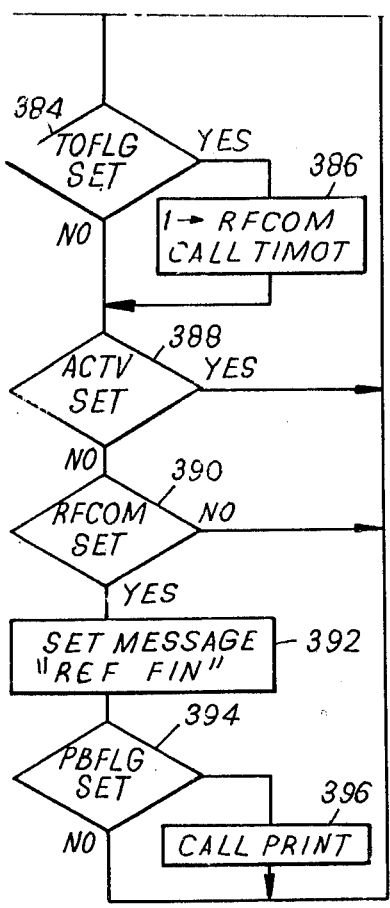
Figure 9:
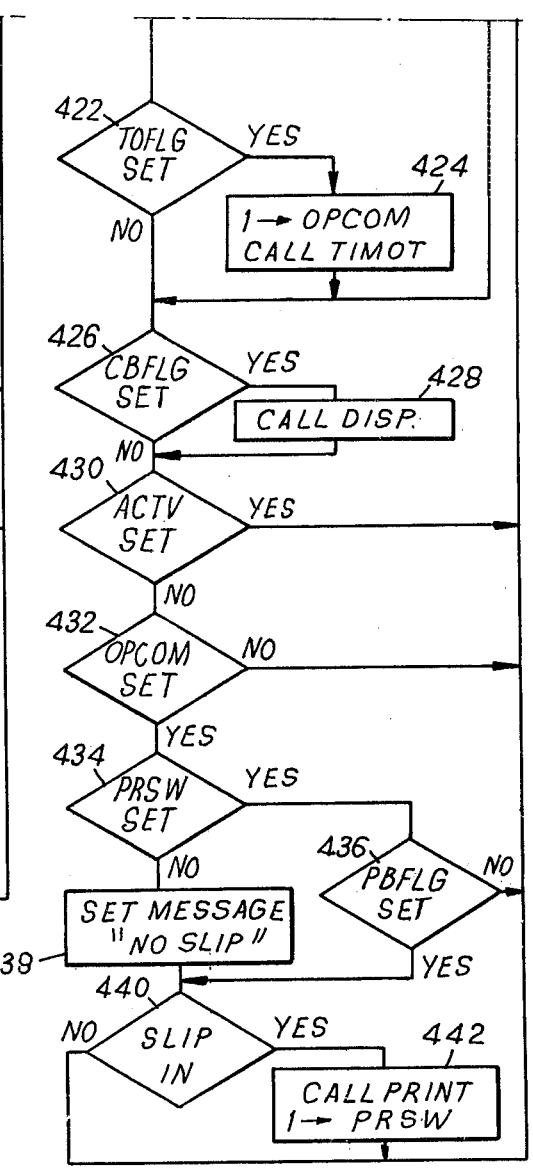

Referring now to REFER program 362 shown in FIG. 8, block 364 indicates that the light beneath the reference button is turned on. This can occur by providing appropriate signals from computer 102 to mode buttons 118. In addition the number "2" is stored in the mode location to indicate the reference mode. Further, block 364 indicates that the time display messages and channel lamps are all turned off and a determination is made whether any tube 22 is inserted in any of the openings 20 and if so the message REMOVE TUBES is turned on.

Next, according to block 366, EVENT program 266 is called for execution and a determination is made whether the FHFLG flag should be set in response to clock 146 providing the signal through status logic 144. Further the depression of mode buttons, if any, is processed and the MBFLG is set, as appropriate.

Next, according to block 368 a determination is made whether the MBFLG is set. If it is, block 370 indicates that it is reset and block 372 indicates that a determination is made whether the ACTV location is set. If ACTV is not set, then block 374 indicates a jump to the MODEC routine 250 in FIG. 5 occurs and the mode button depressed causing the MBFLG to be set is processed by jumping to the appropriate program. However, if at block 372 it is determined that the ACTV location had been set, computer 102 will not allow itself to jump from the reference mode to another mode. As will be explained hereafter, when ACTV is set, analyzer 10 is in the middle of the referencing mode and is inhibited from transfering to the operate or blank modes until the referencing mode has been completed.

Thus, if at block 372 it is determined the ACTV location is set, or if at block 368 it is determined the MBFLG location is not set, then according to block 376 a determination is made whether the FHFLG location is set. If it is, block 378 indicates that FHZ program 444 shown in FIG. 10 is called for execution. In the execution of the FHZ program 444 the insertion of new tubes is checked and if any have been inserted during the preceding ¼ second, the TIFLG location is set. Further after each four executions of the FHZ program 444, that is, after every second, the timeout counters and time display are updated. When a timeout counter is incremented to zero, the TOFLG is set. Further the ACTV location is maintained set so long as any of the timeout counters is not zero.

Figure 11:
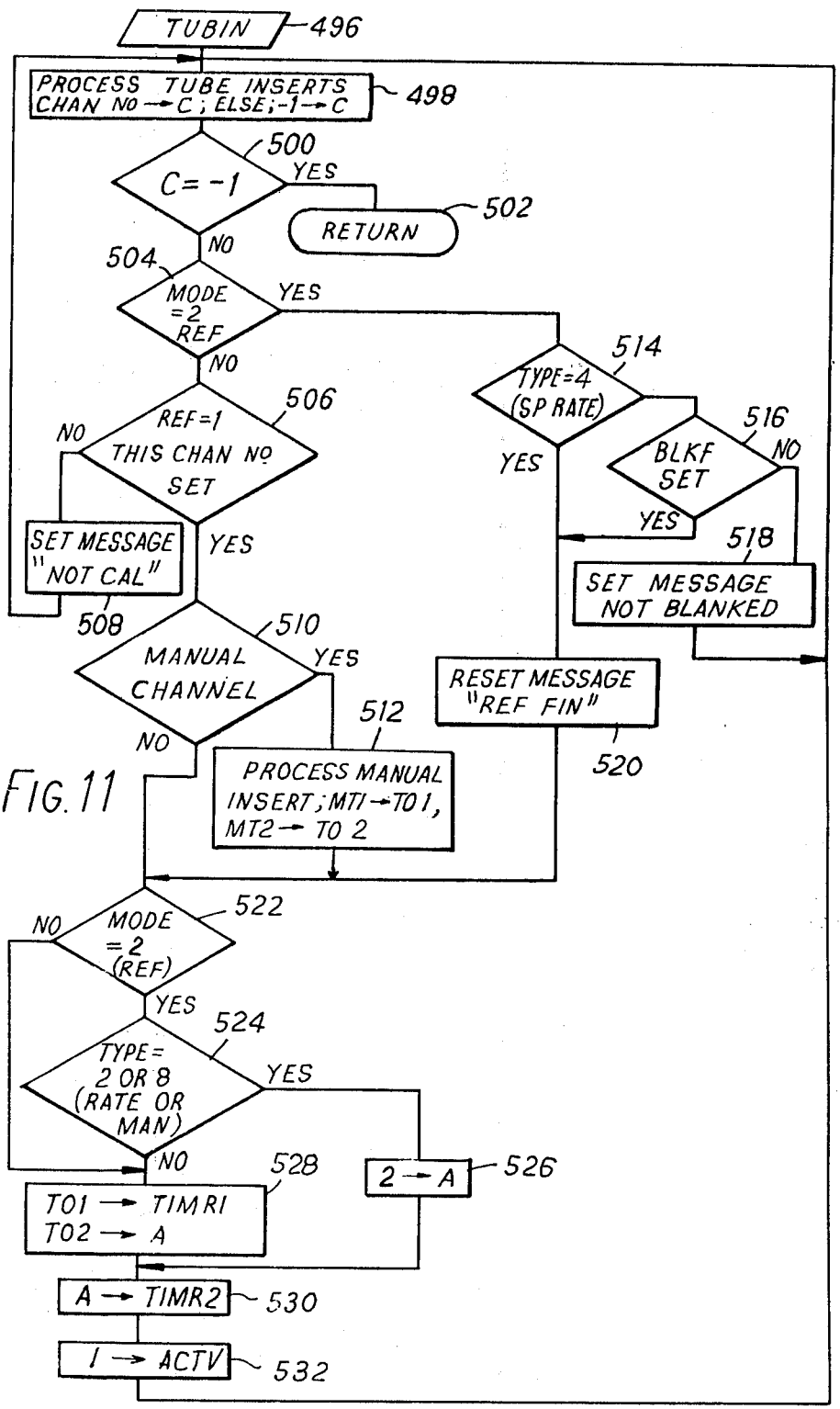

Next according to block 380 a determination is made whether the TIFLG is set. If it is, block 382 indicates that TUBIN program 496 shown in FIG. 11 is called for execution. The processing for this program will be explained hereafter in more detail. However, generally, this processing includes providing proper time to the timeout counters TIMR1 and TIMR2 during the referencing and operate modes of operation.

Figure 12A:
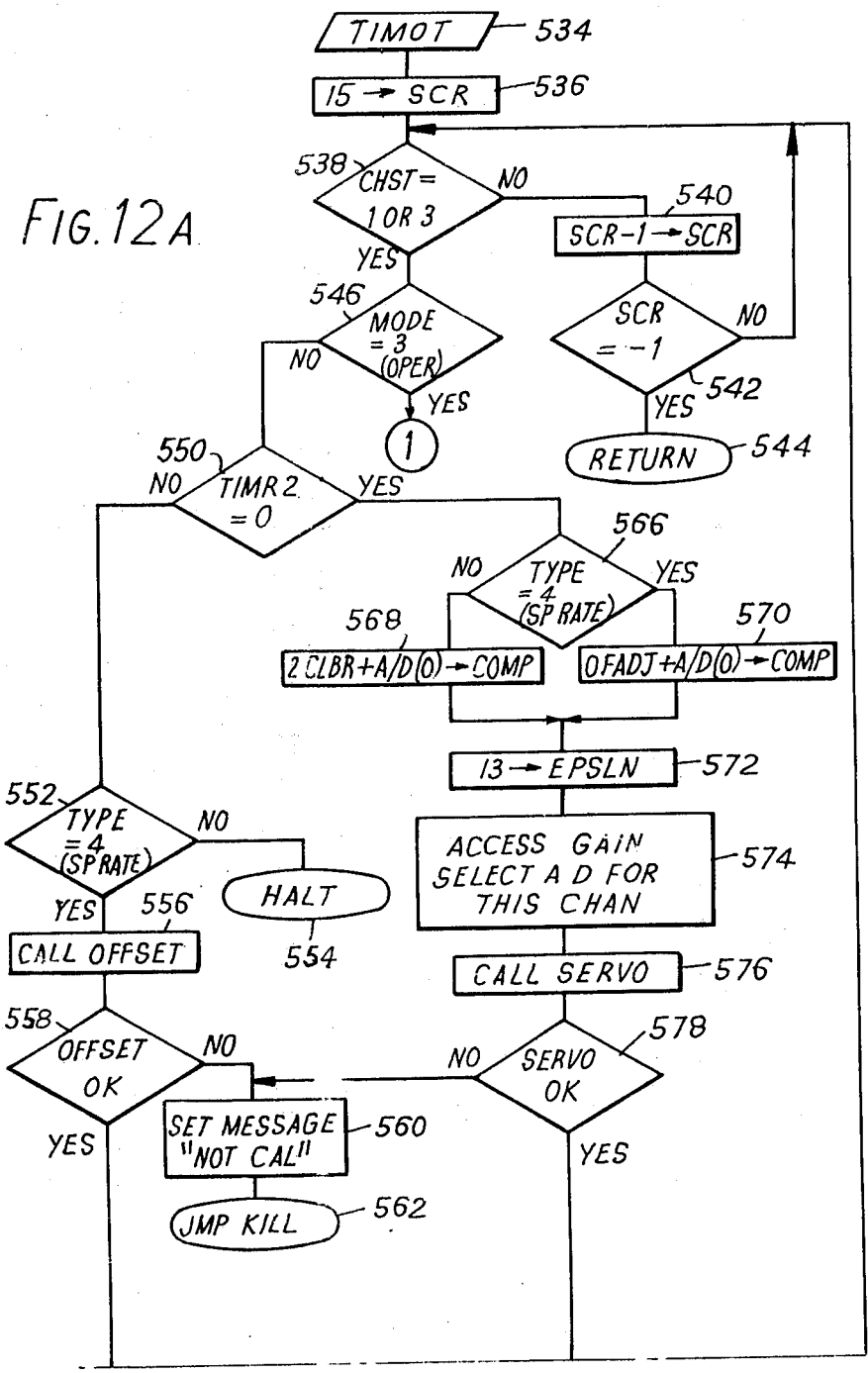
Figure 12A:
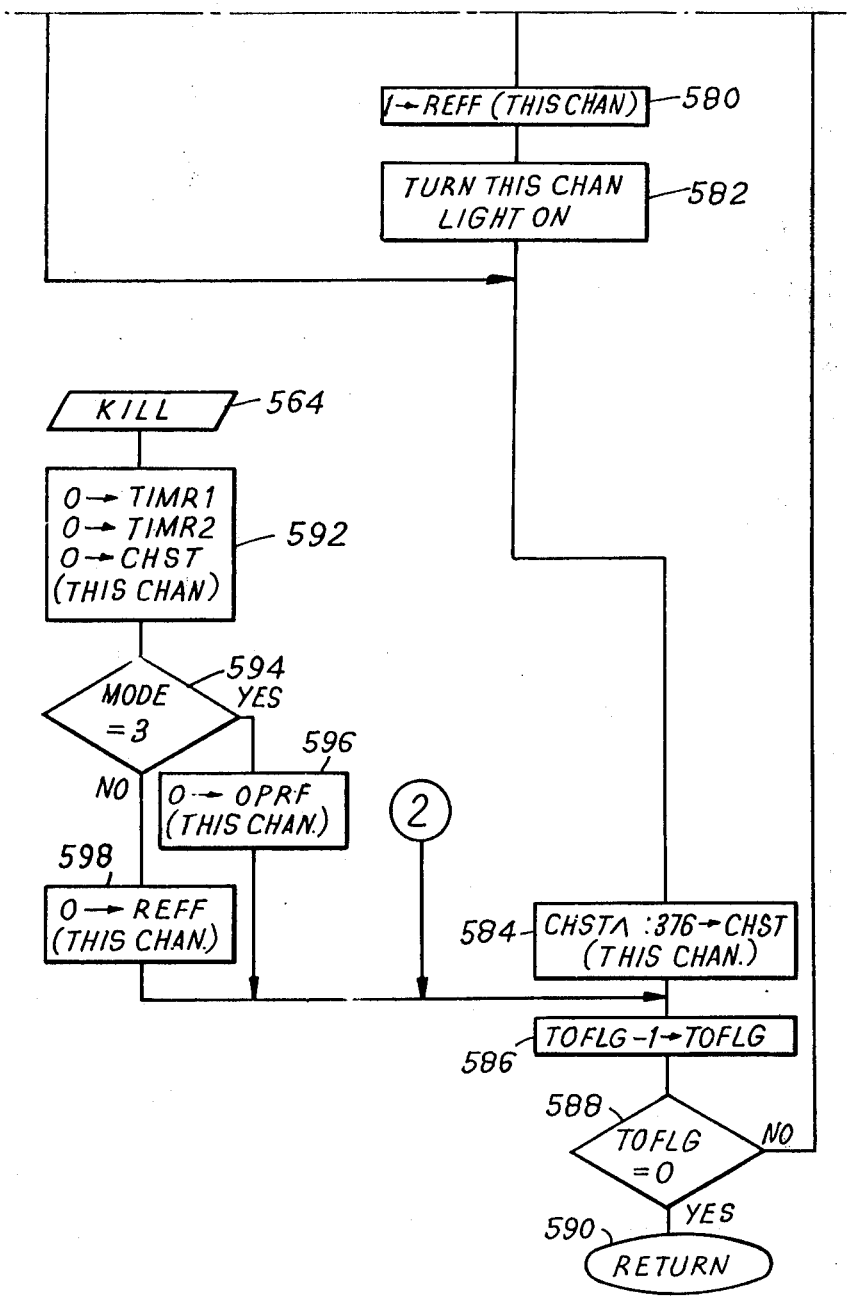
Figure 12B:
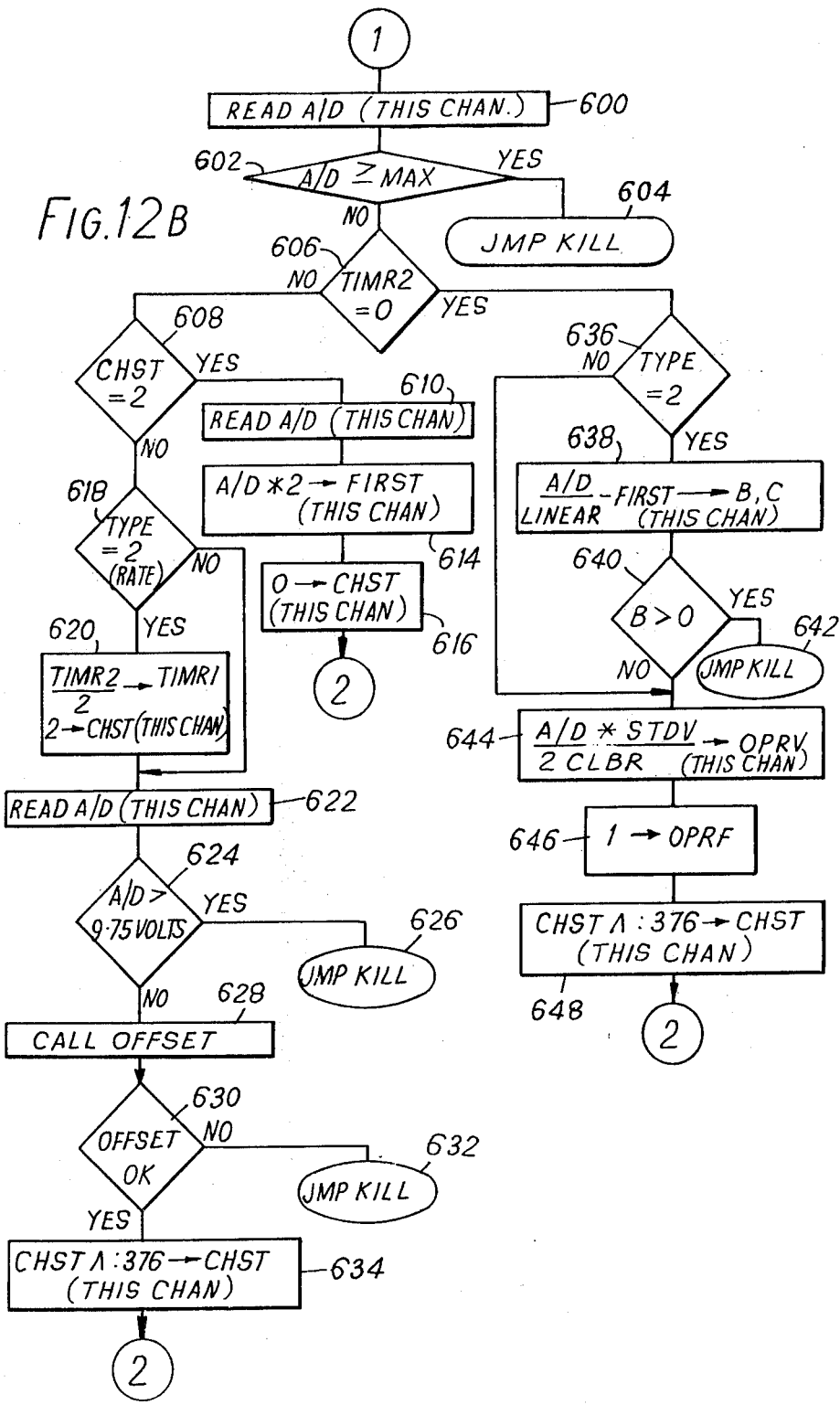

Next, according to block 384 a determination is made whether the TOFLG is set. If it is, block 386 indicates that the RFCOM word is set equal to "1" and TIMOT program 534, shown in FIG. 12A and 12B, is called to execution. The exact details of TIMOT program 534 will be explained in detail hereafter with respective FIG. 12. However, in general, TIMOT program 534 causes the GAIN 1 through GAIN 11 signals to be determined for provision from gain logic 140 analog-to-digital converter 138. These GAIN signals provide the compensation for component variations in the system.

After the TIMOT program 534 execution or if the TOFLG is not set, block 388 indicates a determination is made whether the ACTV location is set. If ACTV is set, a return to block 366 occurs and the above described processing is repeated. However, after the ACTV location is no longer set at this time, which occurs during the execution of FHZ program 444 when both the TIMR1 and TIMR2 counters for all channels are in zero, block 390 indicates that a determination is made whether RFCOM set. If not, a return to block 366 occurs.

If RFCOM is set, then block 392 indicates that the message REF FIN, indicating the referencing mode is completed is caused to be displayed on message display 116 in response to appropriate signals from computer 102 to message display 116.

Then, according to block 394 a determination is made whether the PBFLG location was set during the execution of FHZ program 444. If it was, then according to block 396, the PRINT routine is called and the results determined for the GAIN word may be printed after the execution of the PRINT routine. If the PBFLG location is not set, a return to block 366 occurs and the just described procedure again occurs.

Thus, it is seen that the REFER program 362 is a continuous loop through block 366 and the only way to exit from the REFER program 362 is by depressing a mode button, thereby causing the MBFLG location to be set and existing through block 374 to the MODEC routine 250 shown in FIG. 5.

Referring now the OPRTE program 398, which is executed in response to the depression of the operate button of mode button circuit 118, as indicated at block 262 in FIG. 5, block 400 indicates that first the light beneath the operate mode button is turned on and the other lights turned off. In addition, the number "3" is stored in the MODE location of computer 102 memory and the time display messages and channel lamps are all turned off. In addition, a determination is made whether all the tubes have been removed from the openings 20 and, if not, the REMOVE TUBES message is turned on. Further, the locations PRSW and OPCOM are cleared. As are the OPRV and OPRF tables, which contain a word for each of the sixteen channels.

Next according to block 402, EVENT program 266 is called and MBFLG and FHFLG are set, as appropriate.

A determination at block 404 is made whether the MBFLG is set. If MBFLG is set block 406 indicates that it is cleared and a determination is made at block 408 whether the ACTV flag is set, thereby indicating that the operate mode had not been completed for the test then in process. If at block 408 it is determined the ACTV flag is not set, then block 410 indicates a jump to MODEC routine 250 occurs and a jump from there to the appropriate program indicated by blocks 254, 258 and 262 will occur.

If at block 408 it was determined the ACTV flag was set or if at block 404 it was determined the MBFLG flag was not set, then block 412 indicates a determination is made whether the FHFLG is set. If it is, the FHZ program 444, shown in FIG. 10, is called for execution, as indicated by block 414. As previously mentioned, during this execution, the TIFLG and TOFLG flags are set in appropriate circumstances.

After FHZ program 444 is executed, or if the FHFLG flag is not set, block 416 indicates a determination is made whether the PRSW flag is set to indicate that results have once been printed for the test then in progress. If the PRSW flag is not set, block 418 indicates a determination is made whether the TIFLG is set and if so, block 420 indicates that TUBIN program 496, shown in FIG. 11, is called for execution. As will be explained with respect to FIG. 11, the TUBIN program 496 causes the appropriate times to be stored in the timeout counters TIMR1 and TIMR2 for the particular channel for which the TIFLG was set.

Next, as indicated by block 422, a determination of whether the TOFLG has been set is made. If it is, block 424 indicates that the OPCOM location is set equal to "1" and the TIMOT program 534, shown in FIG. 12, is called for execution. As will be explained hereafter during the TIMOT program 534, the actual readings from the channel detector circuits 128...130 are taken at the appropriate time, as determined by the TIMR1 and TIMR2 counters for each of and channels. And these readings are processed and the results are calculated and stored for subsequent printing and display.

After the execution of TIMOT program 534 or if TOFLG is determined not to be set, block 426 indicates that a determination is made whether the CBFLG is set. In the event that it is, block 428 indicates that the DISP program is called for execution, which program causes the results determined during the TIMOT program for execution to be displayed on the test display 106, the DISP program may be any known program for causing data stored in a computer memory to be displayed.

Thereafter a determination is made whether the ACTV flag is set as indicated at block 430. If it is, a return to block 402 occurs and the above process continues for the remaining channels.

Once the ACTV flag is reset, thereby indicating that the tests have been finally performed on all of the tubes 22 inserted in the openings 20, block 432 indicates that a determination is made whether the OPCOM flag has been set. It is has not been set, then a return to block 402 occurs. However, if the OPCOM flag is set, block 434 indicates that a determination is made whether the PRSW flag is set. If the PRSW flag is set, then block 436 indicates a determination is made whether the PBFLG flag is set. If not then a return to block 402 occurs. If at block 434, it is determined the PRSW flag has not been set, thereby indicating that the initial printing of the results had not occurred, then block 438 indicates that the message NO SLIP is turned on. Then, block 440 indicates a determination is made whether the slip is in. If at block 436 the PBFLG has been determined to be set, thereby indicating a reprinting was to occur, a continuation at block 440 would have occurred.

At block 440 if it is determined that the slip had not been inserted, a return to block 402 occurs and the above described procedure is repeated. However, if it is determined at block 440 the slip is inserted, then block 442 indicates that the PRINT routine is called, and after the printing, the PRSW location is set equal to "1" to indicate that the results have then been printed.

As with the BLANK program 306 and the REFER program 362, the OPRTE program 398 is a continuous loop through block 402 which calls EVENT program 266 for execution. The only way to exit from the OPRTE program 398 loop is through the setting of MBFLG and the jump from block 410 to the MODEC routine 250.

It should also be noted that once all the results have been printed, it is necessary to again depress the operate button in mode button circuit 118 in order to clear the PRSW and OPCOM flags by a jump from MODEC routing 250 back to OPRTE routine 398. Thus, after the initial printing, OPRTE program 398 is in a state of inactivity with the exception that the last calculated results can again be printed and that nothing else can be done, until a new test run is desired and the operate mode button is depressed.

Referring now to FIG. 10, FHZ program 444 will now be explained. It should be recalled that this program is called in response to the FHFLG flag being set at blocks 332, 378 and 414 in FIGS. 7, 8 and 9 respectively. As previously mentioned, FHZ program 444 sets the TIFLG if any tubes have been inserted during the previous 250 milliseconds. Further FHZ program 444 determines whether either the TIMR1 or TIMR2 timeout counters for any of the channels have been incremented to zero.

Referring now specifically to FHZ program 444, it includes block 446 through 494. According to block 446, the FHFLG flag is reset to "0". Then according to block 448, a determination is made whether any tubes 22 have been inserted in the openings 20 during the preceding 250 milliseconds. If a tube had been inserted, then the TIFLG flag is set. This determination may occur by first providing the ING4 and then ING5 signals to tubes detect logic circuit 132 and looking at the two eight bit words provided over the MD10 through MD17 lines and to determine any change therein from the last determination of these lines. The change may be determined by performing an exclusive OR function in computer 102 between the then provided MDI word and the stored previously provided MDI word.

After the tubes insert determination and any setting of TIFLG flag, block 450 indicates that internal counter QTRC is incremented. Then according to block 452 a determination is made whether the QTRC counter is equal to "0"; if not, block 454 indicates a return to the calling program occurs.

However, if the QTRC counter equals "0", block 456 indicates it is reset to a value of minus four. Then after four more executions of the FHZ program 444, the determination at block 452 will again be that the QTRC counter is again equal to "0", or in other words, blocks 456 through 494 are performed only once every second, whereas blocks 446 through 452 are performed every ¼ second.

Next, according to block 458, a determination is made whether the MODE word is set to a value of "1" (blank mode). If it is, block 460 indicates a return to the calling program occurs; under normal operation, this should never occur. Next, according to block 462, a determination is made whether the ACTV flag is set. If ACTV is set, time display 108 is updated, that is one second is subtracted from the time display thereon. Time display 108 displays the time remaining until the end of the longest test then programmed by the insertion of tubes openings 20.

If at block 462, it had been determined that the ACTV flag was not set, block 464 is skipped. Next, according to block 466 the number "15" is stored in the SCR word and the number "0" is stored in the ACTV flag location thereby resetting it. The SCR word is used as a counter to count the 16 channels 0 through 15 for subsequent determinations of timeouts.

Continuing with block 468, the value of TIMR1 counter associated with the channel number having the SCR value is decremented. Then, according to block 470 a determination is made whether the value stored in the TIMR1 counter is equal to "0". If it is, block 472 indicates that the TOFLG is incremented by "1". However, if at block 470 it was determined that the TIMR1 value was not "0", then block 474 indicates that the ACTV value is set equal to "1" and block 476 indicates that a logical OR function is performed between the channel status value CHST and the octal value 001. It should be noted, the particular CHST word is the one associated with the channel having the SCR value.

It should be noted that the operation of blocks 470, 472, 474 and 476 result with the ACTV value being set, as long as any one of the TIMR1 counters for a particular channel is not equal to "0". It should be noted that the value in TOFLG location can be incremented above one if more than one channel timesout simultaneously.

Continuing with block 478, the value in the TIMR2 counter for the channel having the SCR value is then decremented by one, and at block 480, a determination is made whether a TIMR2 counter is equal to zero. If it is block 482 indicates that TOFLG is incremented by one. However, if the TIMR2 counter is not equal to zero at this time, block 484 indicates that a ACTV is set equal to "1" and a logic OR function is performed between the CHST value and octal 001.

Continuing with block 486, the SCR value is then decremented by one and at block 488, a determination is made whether the SCR value is equal to minus one. If SCR is not equal to minus one, thereby indicating that each of the channels 0 through 15 has not been processed for timeout determinations, a continuation to block 468 as indicated, whereby a timeout determination for the next lower number channel occurs.

If at block 488 it is determined that the SCR value equals minus one then block 490 indicates that a determination is made whether the ACTV value is equal to "0". If it is equal to 0 then block 492 indicates that the time display 108 is cleared. Thereafter, or in the event that the ACTV value is not equal to 0, block 494 indicates that a return to the calling program occurs.

Referring now to FIG. 11, TUBIN program 496 is shown and includes block 498 through 532. This program is called for execution during REFER program 362 at block 382 or during OPRER program 398 at block 420 to process the insertion of a tube 22 in an opening 20. First, as indicated at block 498, the new tube inserted is processed by causing a channel number for that tube to be stored in the C register of computer 102. If no tube had been inserted the number minus one is inserted in the C register. Then, according to block 500, a determination is made whether the value in the C register is equal to minus one. If it is, thereby indicating that no tube had been inserted, then according to block 502 a return to the calling program is indicated.

However, if at block 500 it is determined that the value in the C register is not equal to minus one, then according to block 504 a determination is made whether the value in the MODE location is equal to two (referencing mode). If the MODE value is not equal to two then according to block 506 a determination is made whether the REFF flag for the particular channel number is set. If it is not, then according to block 508, the message NOT CAL is caused to be displayed on message display 116 and a return to block 498 is indicated.

If at block 506 it was determined that the REFF flag was set, then according to block 510 a determination is made whether a tube is inserted in the manual channel. If it has, then according to block 512 this tube insertion is processed and the time MT1 and MT2 set on the manual switches 110, are stored in the respective TO1 and TO2 locations associated with the manual channel.

Referring again to block 504, if it had been determined that the MODE value was equal to two, that is, the reference mode, then according to block 514, the TYPE value is checked to determine if it is equal to four, that is, a special rate reaction. If it is not a special rate reaction, then according to block 516, a determination is made whether the BLKF flag is set. If the BLKF flag is not set, then according to block 518 the message NOT BLANKED is illuminated and a return to block 498 is indicated. If at block 516 the BLKF flag was determined to be set, then according to block 520 the REF FIN message is reset.

After the execution of the block 510, 512 or 520, as the case may be, a continuation with block 522 occurs, where the MODE value is again checked. If the MODE value equals two, that is the referencing mode, then, according to block 524, the TYPE value is checked to determine if it is equal to two or eight, that is a rate or a manual type reaction. If TYPE equals two or eight, then according to block 526, the number "2" is stored in the A register of computer 102. If at block 522 it was determined that the MODE value is not equal to two, thereby indicating that the operate mode is underway, block 524 is skipped. Further if the TYPE value is not equal to two or eight and the MODE value is not equal to two, then block 528 indicates that the value in the TO1 location for that channel having the tube being processed is stored in the TIMR1 location and the value in the TO2 location is stored in the A register of computer 102.

After the execution of block 526 or 528, a continuation with block 530 occurs where the value of the A register is stored in the TIMR2 location of the RAM memory and according to block 532, the ACTV location is set equal to one. Thereafter, a continuation back to block 498 occurs to process any other inserted tubes in the manner just described.

Referring now to FIG. 12, which consists of FIGS. 12A and 12B, a description of TIMOT program 534 will now be given. It should be recalled that TIMOT program 534 is called for execution during the REFER program 362 at block 386 or during the OPRTE program 398 at block 424. In response to the TOFLG value being set equal to one during the execution of the FHZ program 444. TIMOT program 534 consists of blocks 536 through 648.

First according to block 536, the value fifteen is stored in the SCR location to indicate the particular channel 0-15 then being processed. Then, according to block 538, a determination is made whether the channel status CHST value is equal to one or three. If it is not, then according to block 540, the SCR value is decremented and according to block 542, a determination is made whether SCR is equal to minus one. If it is not, a branch back to block 538 occurs. If at block 542 it was determined that the SCR value equalled minus one, then according to block 544 a return to the calling program occurs.

If at block 538 it had been determined that the channel status CHST value was equal to the value of one or three, then according to block 546 a determination is made whether the value in MODE is equal to three or whether the operate mode is then underway. If the operate mode is underway, then a continuation to FIG. 12B at continuation point 1 occurs. However, if the MODE value is not equal to three, that is, it equals two indicating the reference mode, then according to block 550 a determination is made whether the value in the TIMR2 counter is equal to zero indicating a second time out has not occurred. Then continuing to block 552, a determination is made whether the TYPE location is equal to four or that a special rate reaction is being processed. If TYPE does not equal four then an error has occurred in the execution of the program and according to block 554 a halt instruction is executed. It should be noted at this point that for a special rate reaction no blanking occurs during the blank mode and it is therefore necessary for the blanking to occur at this point.

Thus, assuming that at block 552 it was determined that a special rate reaction was underway, then according to block 556 OFFSET program 650 is called for execution and the values of the OFFSET signal are determined in the manner which will be explained in more detail with respect to FIG. 13. Continuing with block 558 a determination is made whether the offset internal check is proper. If it is not, then according to block 560 the message NOT CAL is caused to be illuminated and according to block 562 a jump to the KILL routine 564 occurs.

Referring again to block 550, if it had been determined that the TIMR2 counter equalled 0, that is a second time that was occurring, then according to block 566 a determination is made whether the TYPE location has a value of four therein, thereby indicating a special rate reaction channel was being processed. If TYPE does not equal four then according to block 568 a value equal to 2CLBR plus the value from converter 222 for analog ground is stored in location COMP. It at block 556 a special rate reaction had been determined, then according to block 570 the value in the OFADJ location for this channel plus the digital value for analog ground are stored in the COMP location. The CLBR and OFADJ values for each channel are given in Table 1.

Then according to block 562 octal 013 is stored in the EPSLN location. This value represents the maximum allowed variance to the output signal after GAIN 0 through GAIN 11 signals are provided.

Next, according to block 574, computer 102 is caused to access the GAIN table in RAM memory and the analog-to-digital converter circuitry is selected to read the information from the channel having a number equal to the value in SCR location. This may occur by providing the proper code from computer 102 to channel select logic 136 and causing the proper one of the RL0 through RL15 signals to be provided to the channels 128 . . . 130, thereby closing the switches 152 through 154 in that particular channel. After the analog signal to that particular channel is selected, that is, the switch is closed, block 576 indicates that SERVO program 678, shown in FIG. 14, is called for execution. As will be explained hereafter with respect to FIG. 14, SERVO program 678 calculates the value for the selected GAIN 0 through GAIN 11 signals or the OFFSET0 through OFFSET11 signals. In the case of block 574 the GAIN table had been accessed, so that GAIN 0 through GAIN 11 signals will be determined as previously mentioned. This occurs by setting, from most significant to least significant, one at a time, each of the GAIN signals and determining whether the value provided is less than zero. If it is not, the signal is left set and if the value is less than zero, the signal is reset. In this manner, proper GAIN signals can be determined.

Next, as indicated in block 578, a determination is made whether the SERVO determination of the GAIN signal had been proper. If not, a branch to block 560 occurs, causing the NOT CAL message to be turned on, and according to block 562 a jump to KILL routine 564 occurs.

However, assuming SERVO was proper at block 578, block 580 indicates that a "1" is stored in the REFF location for the channel having the SCR number and block 582 indicates that the channel light beneath the channel button is turned on.

Next, according to block 584 a logical AND function is performed between the value of the channel status CHST word for the particular channel and the octal number 376. This function in block 584 is the same as subtracting one from an odd setting of CHST and leaving unaffected an even setting for CHST.

If at block 550 it had been determined that the offset was OK a branch to block 584 also would occur.

After the logical AND function on the CHST value had been performed, block 586 indicates that the value in location TOFLG is decremented by one and in block 588 the determination is made whether the value in TOFLG location is equal to "0". If it is, block 590 indicates a return to the calling program occurs. If TOFLG is non-zero, then a return to block 538 occurs and the next channel is processed until such time as another timeout channel has been found.

At block 562 a jump to the KILL routine 564 was indicated in the event that the OFFSET or SERVO programs 650 and 678 failed. KILL routine 564 eliminates the particular operation then occurring for that channel. First according to block 592, the TIMR1 and TIMR2 timers are set equal to zero and CHST for that particular channel is set equal to "0". Then according to block 594, a determination of the value in MODE occurs. If it is equal to "3" indicating the operate mode, then the OPRF flag for that particular channel is set equal to "0". If the MODE locations value is not equal to "3", thereby indicating that the reference mode is in progress, then block 598 indicates that the REFF location for the particular channel is set equal to "0". After the execution of either blocks 596 or 598, a continuation at block 586 occurs where the timeout flag TOFLG is decremented.

In summary, during the referencing mode of operation of analyzer 10, the value of the GAIN 0 through GAIN 11 signals is determined to arrive at an output signal equal to the value 2 CALB in the case of an end point or rate reaction, or equal to the value of the OFADJ value in the case of a special rate reaction. Depending upon the particular test these value may be for instance, 5 volts of the 10 volt scale, 2½ volts of the 10 volt scale or 1¼ volts on the 10 volt scale depending upon the particular test. From table 1, given above, where the value of the CLBR table is equal to 12, it manifests a target voltage of 2½ volts where the value is 13, it manifests a target voltage of 5 volts, and where the value is 11, it manifests a voltage of 1¼ volts. The particular, target value voltage is dependent upon the type of a particular reaction involved. It should be noted that the target voltage values referred to are those voltages for which the GAIN signal is adjusted when the analog ground is being measured through multiplexer 210.

After the processing of TIMOT program 534 during the referencing procedure as shown by FIG. 12A, the values of the GAIN 0 through GAIN 11 signals and the OFFSET0 through OFFSET11 signals will be fixed and the unknown sample being measured will be processed using these signals. However, these signals will be calculated with regard to the specific reagents, specific components and the intensity of the radiant energy source so that long term variations of these variables will be eliminated. It should be noted that the referencing and blanking procedures should be periodically performed, such as, at least one time a day and possibly more often, so that variables that can affect the result are short term variables.

Referring now to FIG. 12B, when it is determined at block 546 that the mode value equals "3", that is, the operate mode is then in progress, a branch occurs to point 1 in FIG. 12B. Block 600 indicates that the analog-to-digital converter 222 is read for the particular channel manifested by the SCR value. This occurs by providing the proper code to channel select logic 136, based on the SCR value, and closing the appropriate relays 152 and 154 therein. Thereafter the SIG and REF signals from that particular channel are passed to the log ratio circuit 160 and the filter 162. In performing the reading, indicated in the block 600, the output for the inverse or non-inverse is sent to allow either the ANA SIG or the output of amplifier 166 to pass through multiplexer 164, to amplifier 172, where the analog offset voltage is added and the result is applied to digital-to-analog converter 190, which is affected by the applied GAIN 0 through GAIN 11 signals. Thereafter, multiplexer 210 is selected to pass the output from amplifier 208 to analog-to-digital converter 222.

Next, according to block 602, the output from the analog-to-digital converter 222 is checked to see whether it exceeds a certain maximum value. If it does a jump to KILL routine 564 occurs. However, assuming a valid reading from the analog-to-digital converter 222 occurs, block 606 indicates that a determination is made whether the TIMR2 counter for the particular channel equals "0". If it does not, the set TOFLG causing the calling of this program indicates by elimination that the TIMR1 counter equals "0". Then, according to block 608 a determination is made whether the channel status is equal to "2". If it is, block 610 indicates that the analog-to-digital converter is again read as previously indicated, and according to block 614 the result is multiplied by two and stored in location FIRST for the particular channel. Then, according to block 616, the CHST is set for the particular channel to "0" and the branch to branch point 2 and block 586 in FIG. 12A occurs, where the TOFLG is decremented and processing continues from there.

If at block 608 it had been determined that the CHST did not equal to "2", then block 618 indicates that a determination is made of the type of reaction. If a rate reaction is occurring, it is desired to make a linearity test, as will be explained hereafter. To do this, one half of the value in the TIMR2 counter is stored in the TIMR1 counter and a reading at this time will be taken. Then the value "2" is stored in the CHST location for the particular channel. Thus, blocks 610, 614 and 616 are applicable for the mid-point reading or linearity reading to be taken. If at block 618, it was determined that the type of reaction involved was not a rate reaction, then block 620 is skipped and block 610, 614 and 616 for that particular channel are never executed.

Continuing with block 622, analog-to-digital converter 222 is again read in the manner previously described. Another determination is made at block 624 whether the voltage from analog-to-digital converter 222 is greated than 9.75 volts. If it is, block 626 indicates a jump to KILL routine 564, occurs.

However, assuming a proper analog-to-digital voltage is determined at block 624, block 628 indicates that the OFFSET program 650 is called for execution at this point, and new values for the OFFSET0 through OFFSET11 signals are determined. It should be noted at this point that only a special rate reaction is involved and thus, for only this type of reaction is an offsetting feature accomplished during the first timeout period.

Block 630 indicates that a determination is then made whether the offsetting procedure at block 628 was properly accomplished. If not, block 632 indicates a jump to KILL routine 564. If the offsetting procedure was proper, then block 634 indicates that a logical AND function is performed between the CHST value for that channel and the octal number 376, or in other words, one is subtracted from even number status numbers and odd number channel status numbers are left unaffected. Thereafter a continuation at point 2 in FIG. 12A occurs.

If at block 606 it had been determined that the TIMR2 counter was equal to "0", thereby indicating a second time out, then according to block 636, a determination is made whether a rate reaction is then occurring. If it is a rate reaction, then block 638 indicates the linearity test is undertaken. This test causes the value from analog-to-digital converter 222 read at block 600 to be divided by the LINEAR value stored as shown in Table 1 to be determined and to have the value FIRST, stored at block 614, to be subtracted therefrom. This difference is stored in the B and C registers of computer 102. Then according to block 640, a determination is made whether the four most significant bits of the calculation at block 638 are greater than 0. If yes, a jump to KILL routine 564 occurs. However, if the B register containing the 4 most significant bits is "0", then the linearity test is passed.

If at block 636 it was determined not to be a rate reaction, no linearity test is undertaken and a continuation at block 644 occurs. At block 644, the actual result of the test is determined by multiplying the value from the value read from analog-to-digital converter 222 at block 600 by the value stored in the STDV location for the particular channel, and dividing this product by the number 2 CLBR. The results of this calibration are stored in the OPRV location for the particular channel. It should be recalled that the CLBR number is stored in Table 1. It further should be noted that the STDV value is the value read from the calibration prom during START program 130, shown in FIG. 5.

Next, according to block 646, the OPRF location for this channel is set equal to "1" and according to block 648, a logical AND function is performed on the CHST value for this channel and the octal number 376. Thereafter a return to point 2 in FIG. 12A occurs.

Thus after the execution of the procedure shown in FIG. 12B, the OPRV location for the particular channel will contain the results of the test on the unknown in the desired units. It should be recalled that during the operate loop, the PRINT routine is called and it is the value in the OPRV tables that is printed.

Referring now to FIG. 13, OFFSET program 650 will now be described. First according to block 652, the values in the GAIN location for the particular channel then being processed are saved. Then according to block 654, the arbitrary value octal 02052 for the 12 bits of GAIN are stored in the GAIN table for that particular channel. Then, according to block 656, analog-to-digital converter 222 is read with the analog ground being applied through multiplexer 210. The value read as at block 656 is stored in the location COMP as a target value, as indicated at block 658. In addition the value octal 003 is stored in the location EPSLN as the allowed variance for the offsetting procedure.

Next, according to block 660 the channel then being processed is selected for reading and the analog signal having the arbitrary gain of octal 02042 is read and applied through multiplexer 210. Then, according to block 662, the SRDIR location is set equal to "1" and according to block 644, the OFFST table is accessed.

Next, according to block 666 SERVO program 678 is called for execution, as will be explained hereafter with respect to FIG. 14. SERVO program 678 causes each of the offset signals to be turned on one at a time and then turned off if the results of turning them on causes a negative voltage to be provided from the analog-to-digital converter 222.

Next, according to block 668, the carry value from SERVO routine is saved and according to block 670 the GAIN saved at block 652 is restored. Then, according to block 672 the SRDIR word is reset to zero and according to block 674 the CY value saved at block 668 is restored. Then according to block 676 a return to the calling program occurs.

Referring now to FIG. 14, SERVO program 678 will be described. Before executing SERVO program 672, it is necessary to access a variable, which will either be the OFFSET table or the GAIN table. As used in the description of SERVO program 678, the Term VAR will refer to the particular one of the OFFSET or GAIN tables accessed. Further, prior to performing the SERVO routine, it is necessary that the target value be in the COMP location and the allowed tolerance be stored in the EPSLN location. Further, the particular channel must be selected.

First, according to block 680, the number minus 12 is stored in the SRVAR location to indicate the 12 bits of either the GAIN or OFFSET signals which are being processed. Next, according to block 682, bit 11 of a word MASK is set equal to logic "1" and according to block 684, the accessed variable is set equal 0. Continuing with block 686, a logical OR function is performed between the variable word and the word MASK, with the results being stored back in the variable word. Thus, the first time this occurs, the variable word will have a one in bit 11 thereof.

Then block 688 indicates that the offset and gain values stored are sent to the offset and gain logic circuits 140 and 142. It should be noted that one of these offset and gain words will be the variable. Then the analog-to-digital converter 222 is read for the output of offset and gain values for the particular channel selected.

Then, according to block 690, a determination is made whether the output from analog-to-digital converter 222 is less than 0. If it is less than 0, then block 692 indicates that a logical AND function is performed between the variable and the compliment of the value in MASK location (MASK) and the results stored in the variable. If at block 690 the analog-to-digital converter 222 output had not been less than 0, then block 692 is skipped. Thus, a determination is made whether a particular bit of the variable should be on or off as determined by block 690 and 692 after having read the particular channel with the bit on, as indicated at blocks 686 and 688.

Continuing with block 694, the one bit in the MASK word is then right shifted one position, or in the first instance from bit 11 position to bit 10 position. Thereafter, as indicates at block 696 the value in the SRVAR location is incremented by one. At block 698 a determination is made whether the SRVAR word is equal to "0". If not, a return to block 686 occurs and the above process of checking each bit of the variable is repeated for the bit position corresponding to the "1" bit in the MASK word.

After it is determined that the SRVAR word is equal to 0 at block 698, block 700 indicates that the OFFSET and GAIN values determined are outputted and the analog-to-digital converter is read for the particular channel. Then, according to block 702, a determination is made whether the absolute value of the difference between the target value COMP and the analog-to-digital converter 222 reading is less than the tolerance EPSLN. If the absolute value is less than the EPSLN value, then according to block 704, an "0" is stored in the B register of computer 102. However, if the absolute value is greater than or equal to the EPSLN value, then according to block 706, bit 7 of the B register in computer 102 is set equal to "1". Thereafter, according to block 708, the contents of B register is transferred to the A register which is then rotated through the carry storage location within computer 102. In this manner, the carry storage manifests whether or not the result of the SERVO operation provided an answer within the tolerance set forth in the EPSLN word.

Therafter according to block 710 a return to the calling program occurs.

I claim:

1. In a spectrophotometric measuring system for analyzing the concentration of a substance in a sample as a function of optical density of the sample, calibration means comprising first and second photodetectors positioned for respectively receiving radiant energy of a source and radiant energy applied from the source through a sample; ratio means connected to said photodetectors for providing an output as a function of the ratio of the outputs of said first and second detectors; a programmable voltage source; summing amplifier means having outputs from said ratio circuit and from said programmable voltage source coupled thereto for summing the outputs thereof, measuring means for measuring an output indicative of the output of said summing amplifier; a progammable gain amplifier coupled between said programmable voltage source and said measuring means; control means connected to said measuring means, and providing outputs coupled to program said programmable voltage source and said programmable gain amplifier; blank mode selection means for selection in correspondence with placing of a blank sample between said source and said second photodetector for connecting said control means for setting gain of said programmable gain amplifier at a preselected level and for providing a programming signal to said programmable voltage source; said control means further comprising blank level means for providing a value indicative of a desired blank level; means for comparing the output of said summing means to the output of said blank level means and for providing the programming signal to reduce the error between the value and the output of said summing means below a predetermined level, and means for holding and applying said programming signal to said programmable voltage source in an operate mode in which an unknown sample is placed between the source and said second photodetector.

2. Apparatus according to claim 1 further comprising reference mode selection means for selection in correspondence with placing a reference sample between said source and said second photoconductor for connecting said control means for providing the programming signal to said programmable voltage source and for determining a gain control signal for said programmable gain amplifier; said control means further comprising storage means for storing a preset value indicative of a desired signal to be obtained from said measuring means in response to placing of the reference sample between said source and said second photodetector, and wherein said means for comparing further comprises means for comparing the output of said measuring means to said preset value and for providing the gain control signal to reduce the difference between the output of said measuring means and the desired signal below a predetermined level, and means for holding and applying said gain control signal to said programmable gain amplifier in an operate mode, whereby resolution of said measuring system is improved.

3. Apparatus according to claim 2 wherein said ratio circuit comprises a log ratio circuit.

4. Apparatus according to claim 3 wherein said blank level means comprises means for providing a value indicative of analog ground.

5. Apparatus according to claim 4 comprising a plurality of first and second photodetectors, each pair of first and second photodetector being associated with one channel, first multiplexing means for multiplexing channel outputs to said ratio circuit, second multiplexing means synchronized with said first multiplexing means for operating said control circuit for individually processing outputs of said measuring means for producing the programming signal and gain control signal for each channel when operating in the blank mode and reference mode respectively.

6. Apparatus according to claim 5 wherein said control means further comprises means for storing each programming and gain control signal for each channel.

7. Apparatus according to claim 6 wherein said control means further comprises accessing and multiplexing means synchronized with said first multiplexing means for accessing during an operate mode programming and gain control signals corresponding to the channel for which outputs are provided from the first and second photodetectors to said ratio circuit and coupling the programming and gain control signals to said programmable voltage source and programmable gain amplifier respectively; and further comprising means for clearing said programming and gain control signals to enable application of programming and gain control signals corresponding to another channel to said programmable voltage source and said programmable gain amplifier.

8. Apparatus according to claim 7 wherein said measuring means comprises an analog-to-digital converter for supplying output signals to a digital register.

9. Apparatus according to claim 8 wherein said programmable voltage source comprises a digital-to-analog converter and said programming signal comprises a digital word having respective bits coupled to successive stages of said digital-to-analog converter.

10. Apparatus according to claim 9 wherein said programmable gain amplifier comprises a digital-to-analog converter coupled to an operational amplifier for determining the gain thereof and said gain control signal is a digital word having respective bits coupled to successive stages of said digital-to-analog converter.

* * * * *